(12) United States Patent  
Kishimoto et al.

(10) Patent No.: US 7,722,543 B2
(45) Date of Patent: May 25, 2010

(54) BLOOD PRESSURE MEASURING DEVICE

(75) Inventors: Hiroshi Kishimoto, Kyoto (JP); Masayuki Fukutsuka, Uji (JP); Kenji Eda, Suita (JP); Takahide Tanaka, Otsu (JP); Yosuke Fujii, Takatsuki (JP)

(73) Assignee: Omron Healthcare Co., Ltd., Kyoto (JP)

( * ) Notice: Subject to any disclaimer, the term of this patent is extended or adjusted under 35 U.S.C. 154(b) by 740 days.

(21) Appl. No.: 11/502,394

(22) Filed: Aug. 11, 2006

(65) Prior Publication Data

US 2007/0038133 A1 Feb. 15, 2007

(30) Foreign Application Priority Data

Aug. 12, 2005 (JP) .............................. 2005-235009

(51) Int. Cl.
*A61B 5/02* (2006.01)
(52) U.S. Cl. ...................................... 600/485; 600/490
(58) Field of Classification Search ................ 242/371, 242/389; 600/499, 485
See application file for complete search history.

(56) References Cited

U.S. PATENT DOCUMENTS

| | | | | |
|---|---|---|---|---|
| 3,621,845 | A | * | 11/1971 | Oates .......................... 600/490 |
| 3,762,411 | A | | 10/1973 | Hazen et al. |
| 3,777,840 | A | * | 12/1973 | Botnick et al. .............. 280/803 |
| 4,417,703 | A | | 11/1983 | Weinhold |
| 4,768,546 | A | | 9/1988 | Brusadin et al. |
| 5,236,143 | A | | 8/1993 | Dragon |
| 6,068,601 | A | | 5/2000 | Miyazaki et al. |
| 6,322,517 | B1 | | 11/2001 | Yamamoto et al. |
| 6,616,080 | B1 | * | 9/2003 | Edwards et al. .......... 242/378.1 |
| 6,731,956 | B2 | * | 5/2004 | Hanna et al. ............. 455/569.1 |
| 6,799,808 | B1 | | 10/2004 | Walters |
| 2002/0095091 | A1 | * | 7/2002 | Che et al. .................... 600/490 |
| 2003/0146332 | A1 | | 8/2003 | Vinding |

FOREIGN PATENT DOCUMENTS

| | | |
|---|---|---|
| DE | 101 28 337 A1 | 1/2003 |
| EP | 1 048 266 A1 * | 11/2000 |
| EP | 1 048 266 A1 | 11/2000 |
| EP | 1 125 551 | 8/2001 |
| EP | 1 394 094 A2 | 3/2004 |

(Continued)

OTHER PUBLICATIONS

European Office Action dated May 22, 2007, directed to counterpart EP Application No. 06016579.2 with Partial European Search Report.

(Continued)

*Primary Examiner*—Patricia C Mallari
(74) *Attorney, Agent, or Firm*—Morrison & Foerster LLP

(57) ABSTRACT

A blood pressure monitor includes a cuff having an air bag, a main-unit casing in which an inflation/deflation mechanism for inflating/deflating the air bag is provided, a flexible air tube connecting the air bag and the inflation/deflation mechanism, and a retractor unit capable of drawing in the air tube that is drawn out from the main-unit casing into an air tube housing provided in the main-unit casing. With this structure, the blood pressure monitor can be made superior in housing of the air tube connecting the cuff and the main-unit casing.

14 Claims, 23 Drawing Sheets

FOREIGN PATENT DOCUMENTS

| | | |
|---|---|---|
| EP | 1 547 517 A1 | 6/2005 |
| JP | 62-130606 U | 8/1987 |
| JP | 64-019403 U | 1/1989 |
| JP | 03-097443 A | 4/1991 |
| RU | 2 190 345 C2 | 10/2002 |
| TW | 336163 | 7/1998 |

OTHER PUBLICATIONS

Russian Office Action dated Jul. 9, 2007, directed to counterpart Russian Application 2006129230 (4 pages).

Extended European Search Report dated Jul. 26, 2007, directed to counterpart EP Application No. 06016579.2 (16 pages).

* cited by examiner

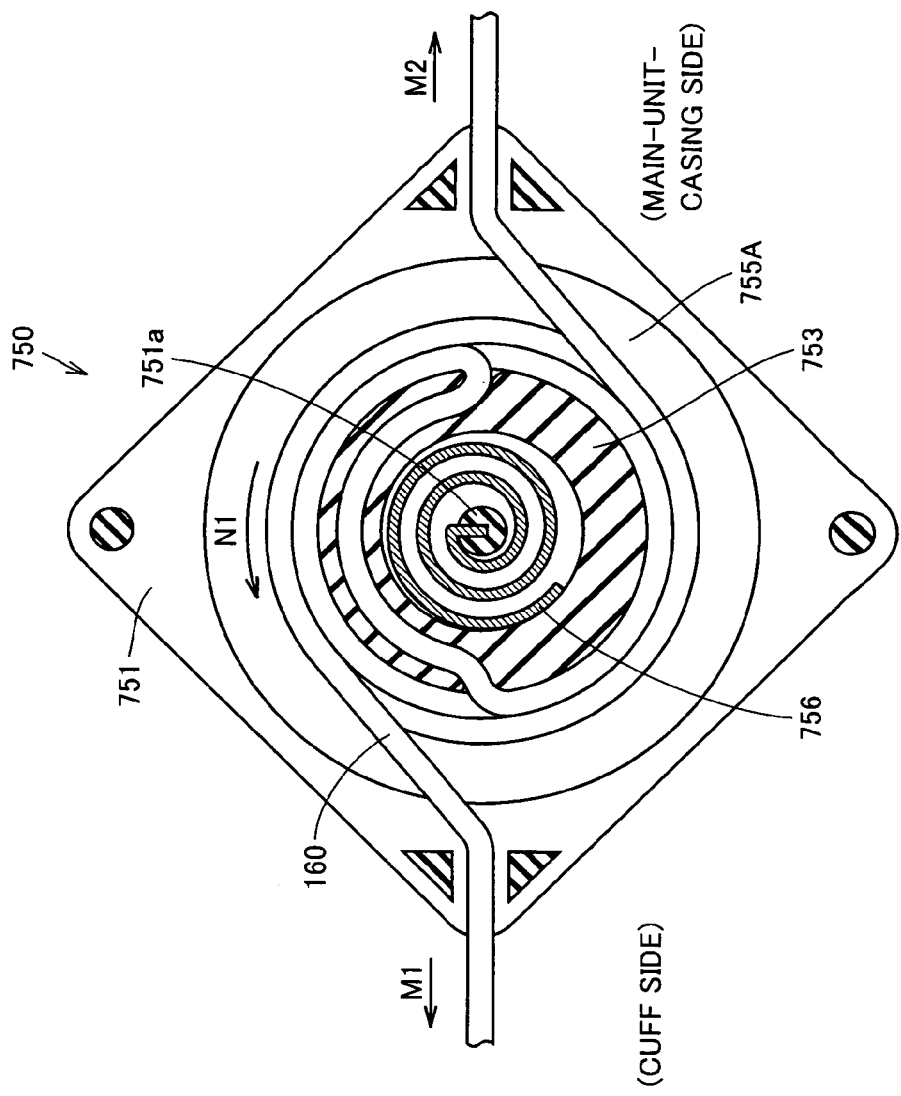
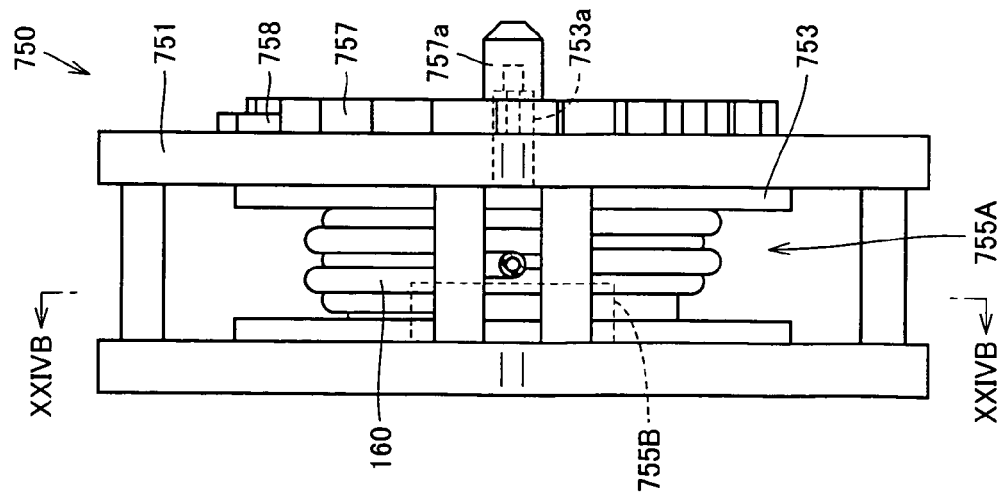

BLOOD PRESSURE MEASURING DEVICE

BACKGROUND OF THE INVENTION

1. Field of the Invention

The present invention relates to a blood pressure measuring device (hereinafter also referred to simply as blood pressure monitor) having a cuff and a main-unit casing connected by a flexible connection tube.

2. Description of the Background Art

Recently, for early detection of lifestyle-related diseases whose main cause is hypertension or for blood pressure management, blood pressure monitors that can be used at home have become widespread. Usually, to measure a blood pressure value, a cuff including a fluid bag for pressing an artery located within a living body is wrapped around the body surface of the living body, and arterial pressure pulse waves caused in the artery by inflation and deflation of the wrapped fluid bag are detected to measure the blood pressure value.

Here, the cuff refers to a band-shaped structure that has a bladder and that can be wrapped around a part of a living body, for use in measurement of arterial pressure of an upper limb/lower limb by supplying such a fluid as gas or liquid into the bladder. Thus, the cuff is a term representing the concept including the fluid bag as well as a mechanism for wrapping the fluid bag around a part of the living body, and the cuff is also called arm band or manchette depending on the case.

For the so-called upper-arm blood pressure monitor using an upper arm as a site for taking a measurement, the structure is employed that connects, by an air tube which is a flexible connection tube, a main-unit casing in which for example a pump and a valve are provided that are components of an inflation/deflation mechanism for inflating/deflating an air bag serving as the fluid bag, and a cuff containing the air bag. Therefore, preferably the upper-arm blood pressure monitor is superior in terms of housing of these cuff, air tube and main-unit casing while the monitor is not in use, and it is required that the components can be housed compactly and that the act of housing the components is easy.

As examples of the upper-arm blood pressure monitor improved in terms of housing, those disclosed in Japanese Patent Laying-Open No. 03-097443 (hereinafter referred to as Document 1), Japanese Utility Model Laying-Open No. 64-019403 (hereinafter Document 2) and Japanese Utility Model Laying-Open No. 62-130606 (hereinafter Document 3) are known.

Document 1 discloses a blood pressure monitor using the Korotkoff method that is structured in the manner that a microphone serving as a detection unit provided in a cuff and a signal processing unit provided within a main-unit casing are connected by a signal line, an air tube serving as a connection tube connecting an air bag and an inflation/deflation mechanism and the signal line are formed as a composite tube where the air tube and the signal line are provided in parallel, and the composite tube is thermally processed into a spiral shape so that the composite tube is elastic and resilient. While the blood pressure monitor is not used, the cuff is housed in a cuff housing provided in the main-unit casing, and the composite tube including the air tube is housed in a composite tube housing provided in parallel with the cuff housing.

Further, Document 2 discloses a blood pressure monitor having a housing box prepared to separately contain a main-unit-casing housing which houses a main-unit casing and a cuff housing which houses a cuff, and these housings are connected to each other via a hinge. While the blood pressure monitor is not used, the main-unit casing is housed in the main-unit-casing housing and the cuff and an air tube are housed in the cuff housing.

Furthermore, Document 3 discloses a blood pressure monitor having a cuff housing case for housing a cuff that is provided in parallel with a main-unit casing, and the main-unit casing and the cuff housing case are structured in the manner that an opening for placing/removing the cuff in/from the cuff housing case takes two states, namely the state where the opening is covered with the main-unit casing and the state where the opening is not covered with the main-unit casing. While the blood pressure monitor is not used, the cuff and an air tube are housed in the cuff housing case and the cuff-housing case is attached to the main-unit casing in the manner that the opening for placing/removing the cuff in/from the cuff housing case is covered with the main-unit casing.

Other than the blood pressure monitors disclosed in Documents 1 to 3, blood pressure monitors improved in terms of housing in various ways are also known. However, many of them merely have, in a main-unit casing, a cuff housing for housing a cuff. Regarding the air tube, it is merely intended that the air tube is folded to be housed in an air-tube housing that is provided in parallel with the cuff housing or the folded air tube is inserted into and held in a hollow portion of a tubular cuff.

As described above, although the conventional blood pressure monitors are improved in various ways in terms of housing of the cuff as disclosed in Documents 2 and 3, almost no improvement has been made for the housing of the air tube. Thus, the user is entirely responsible for the act of housing the air tube. If the user handles the air tube carelessly, the air tube could be bent, twisted or caught between the main-unit casing and the open/close cover. In such a case, at the worst, the air tube could be broken.

In comparison with this, in the case where the structure disclosed in Document 1 is employed, since the composite tube including the air tube is thermally processed to have resilience in spiral manner, it is unlikely that the composite tube including the air tube is bent or twisted. However, if the composite tube is handled carelessly, the composite tube could be caught between the main-unit casing and the open/close cover, which could lead to breakage as well. Further, in the case where the structure as disclosed in Document 1 is employed, the resilience of the composite tube which is thermally processed into the spiral shape always exerts tension on the upper arm while the cuff is mounted on the upper arm. Thus, the accuracy in measurement could be adversely influenced or the user has to bear some inconvenience.

SUMMARY OF THE INVENTION

An object of the present invention is to provide a blood pressure measuring device superior in housing of a connection tube connecting a cuff and a main-unit casing, particularly in ease of handling of the connection tube.

According to a first aspect of the present invention, a blood pressure measuring device includes: a cuff having an inflatable/deflatable fluid bag; a main-unit casing having therein disposed an inflation/deflation mechanism inflating/deflating the fluid bag; a flexible connection tube connecting the fluid bag and the inflation/deflation mechanism; and a retraction mechanism capable of drawing in the connection tube that is drawn out from the main-unit casing, into a connection tube housing provided in the main-unit casing.

With this structure, the connection tube is easily and surely housed, by the retraction mechanism, in the connection tube housing provided in the main-unit casing. Thus, the blood pressure measuring device can be made superior in housing of the connection tube, particularly in ease of handling of the connection tube. Further, since the connection tube is housed in the main-unit casing by the retraction mechanism, it can be prevented that the connection tube is bent or twisted for example to be broken.

Regarding the blood pressure measuring device according to the first aspect of the invention, preferably the retraction mechanism has a wound member on which the connection tube that is drawn in into the connection tube housing is wound.

With this structure, the connection tube in the state of being wound on the wound member is compactly housed in the connection tube housing. Thus, increase in size of the retraction mechanism can be prevented. Further, the relatively simple structure can be used to form the retraction mechanism. Furthermore, since the wound member is used for housing the connection tube, the draw-out/draw-in operation can easily be implemented.

Regarding the blood pressure measuring device according to the first aspect of the invention, preferably the retraction mechanism has an elastic member coupled to the wound member and, in this case, preferably elastic force of the elastic member rotationally drives the wound member and thereby causes the connection tube to be drawn in into the connection tube housing.

With this structure, the elastic force of the elastic member can be used to draw in the connection tube. Thus, the blood pressure measuring device can be made superior in ease of handling of the connection tube.

Regarding the blood pressure measuring device according to the first aspect of the invention, preferably a connection tube locking mechanism is further provided that locks the connection tube against the elastic force of the elastic member.

With this structure, the connection tube drawn out from the main-unit casing to an arbitrary extent can be locked by the connection tube locking mechanism. Thus, the blood pressure measuring device can be made superior in convenience. Further, in the state where the connection tube is drawn out and the cuff is mounted on a site where a measurement is taken, it is prevented that the elastic force of the elastic member exerts tension on the site for taking a measurement. Thus, the accuracy in measurement can be kept high and the user has to bear no burden.

Regarding the blood pressure measuring device according to the first aspect of the invention, preferably the retraction mechanism has a drive unit coupled to the wound member and, in this case, preferably drive force of the drive unit rotationally drives the wound member and thereby causes the connection tube to be drawn in into the connection tube housing.

With this structure, the drive force of such a drive unit as motor can be used to draw in the connection tube. Thus, the blood pressure measuring device can be made superior in ease of handling of the connection tube.

Regarding the blood pressure measuring device according to the first aspect of the invention, preferably the drive unit and the wound member also function as a feed unit feeding the connection tube housed in the connection tube housing, to the outside of the main-unit casing.

With this structure, the drive unit can be used to not only draw in the connection tube but also draw out the connection tube. Thus, the blood pressure measuring device can be made further superior in ease of handling of the connection tube.

Regarding the blood pressure measuring device according to the first aspect of the invention, preferably the retraction mechanism has a rotational operation unit coupled to the wound member and, in this case, preferably rotational operation of the rotational operation unit rotationally drives the wound member and thereby causes the connection tube to be drawn in into the connection tube housing. Here, the rotational operation unit refers to an operation unit structured to be operated by the user for rotationally driving the wound member and includes, for example, handle-type operation unit, jog-dial type operation unit and an operation unit simply formed of a rotation plate, for example.

With this structure, the rotational operation unit can be rotated to easily draw in the connection tube. Thus, the blood pressure measuring device can be made superior in ease of handling of the connection tube.

Regarding the blood pressure measuring device according to the first aspect of the invention, preferably the rotational operation unit and the wound member also function as a feed unit feeding the connection tube housed in the connection tube housing, to the outside of the main-unit casing.

With this structure, the rotational operation unit can be rotated to not only draw in the connection tube but also draw out the connection tube. Thus, the blood pressure measuring device can be made further superior in ease of handling of the connection tube.

Regarding the blood pressure measuring device according to the first aspect of the invention, preferably the main-unit casing has a cuff housing for housing the cuff, and a turning open/close cover attached to cover the cuff housing, and preferably the retraction mechanism has a rotational force transmission mechanism transmitting rotational force that is generated as the open/close cover is turned, to the wound member. In this case, preferably turning operation of the open/close cover rotationally drives the wound member and thereby causes the connection tube to be drawn in into the connection tube housing.

With this structure, in accordance with closing of the open/close cover, the connection tube can be drawn in. Thus, the blood pressure measuring device can be made superior in ease of handling of the connection tube.

Regarding the blood pressure measuring device according to the first aspect of the invention, preferably the open/close cover, the rotational force transmission mechanism and the wound member also function as a feed unit feeding the connection tube housed in the connection tube housing, to the outside of the main-unit casing.

With this structure, in accordance with the turning operation of the open/close cover, not only the operation of drawing in the connection tube but also the operation of drawing out the connection tube can be accomplished. Thus, the blood pressure measuring device can be made further superior in ease of handling of the connection tube.

Regarding the blood pressure measuring device according to the first aspect of the invention, preferably the retraction mechanism has a housing mechanism housing the connection tube in meandering state that is drawn in into the connection tube housing.

With this structure, the connection tube in meandering state can compactly be housed in the connection tube housing. Thus, increase in size of the retraction mechanism can be prevented and the relatively simple structure can be used to form the retraction mechanism.

Regarding the blood pressure measuring device according to the first aspect of the invention, preferably the retraction mechanism has an elastic member coupled to the housing mechanism and, in this case, preferably elastic force of the elastic member drives the housing mechanism and thereby causes the connection tube to be drawn in into the connection tube housing.

With this structure, the elastic force of the elastic member can be used to draw in the connection tube. Thus, the blood pressure measuring device can be made superior in ease of handling of the connection tube.

Regarding the blood pressure measuring device according to the first aspect of the invention, preferably a connection tube locking mechanism is further provided that locks the connection tube against the elastic force of the elastic member.

With this structure, the connection tube drawn out from the main-unit casing to an arbitrary extent can be locked by the connection tube locking mechanism. Thus, the blood pressure measuring device can be made superior in convenience. Further, in the state where the connection tube is drawn out and the cuff is mounted on a site for taking a measurement, it is prevented that the elastic force of the elastic member exerts tension on the site for taking a measurement. Thus, the accuracy in measurement can be kept high and the user has to bear no burden.

Regarding the blood pressure measuring device according to the first aspect of the invention, preferably the retraction mechanism has a drive unit coupled to the housing mechanism and, in this case, preferably drive force of the drive unit drives the housing mechanism and thereby causes the connection tube to be drawn in into the connection tube housing.

With this structure, the drive force of such a drive unit as motor can be used to draw in the connection tube. Thus, the blood pressure measuring device can be made superior in ease of handling of the connection tube.

Regarding the blood pressure measuring device according to the first aspect of the invention, preferably the main-unit casing has a guide mechanism guiding the connection tube and, in this case, preferably the guide mechanism, the drive unit and the housing mechanism function as a feed unit feeding the connection tube housed in the connection tube housing, to the outside of the main-unit casing.

With this structure, the drive unit can be used to not only draw in the connection tube but also draw out the connection tube. Thus, the blood pressure measuring device can be made further superior in ease of handling the connection tube.

Regarding the blood pressure measuring device according to the first aspect of the invention, preferably the main-unit casing has a catch portion by which the connection tube is caught, and a slide lever coupled to the catch portion and, in this case, preferably, as the slide lever is slid, the catch portion is moved to draw in the connection tube into the connection tube housing.

With this structure, the slide lever can be slid to easily draw in the connection tube. Thus, the blood pressure measuring device can be made superior in ease of handling of the connection tube.

Regarding the blood pressure measuring device according to the first aspect of the invention, preferably the main-unit casing has a guide mechanism guiding the connection tube and, in this case, preferably the guide mechanism, the catch portion, the slide lever, and the housing mechanism function as a feed unit feeding the connection tube housed in the connection tube housing, to the outside of the main-unit casing.

With this structure, the slide lever can be slid to not only draw in the connection tube but also draw out the connection tube. Thus, the blood pressure measuring device can be made further superior in ease of handling of the connection tube.

Regarding the blood pressure measuring device according to the first aspect of the invention, preferably an opening provided in the main-unit casing for drawing out the connection tube is opened toward a front side of the main-unit casing.

Usually, the user using the blood pressure monitor is positioned on the front side of the main-unit casing. Accordingly, the direction in which the connection tube is drawn out can be the frontward direction of the main-unit casing. Thus, the blood pressure monitor can be made superior in ease of use.

Regarding the blood pressure measuring device according to the first aspect of the invention, in the case where the cuff is to be mounted on a left upper arm portion of a subject, preferably the opening is provided at a central portion or a left-side portion of the main-unit casing as the main-unit casing is seen from the front side. Further, regarding the blood pressure measuring device according to the first aspect of the invention, in the case where the cuff is to be mounted on a right upper arm portion of a subject, preferably the opening is provided at a central portion or a right-side portion of the main-unit casing as the main-unit casing is seen from the front side.

With this structure, when the cuff is mounted for example, the connection tube is not an obstacle, which is convenient for the user.

Regarding the blood pressure measuring device according to the first aspect of the invention, preferably the main-unit casing has, at its front portion, a cuff housing for housing the cuff and, in this case, the opening is provided in the cuff housing.

With this structure, the opening for drawing out the connection tube can be provided together with the cuff housing in the front portion of the main-unit casing. Thus, it is easy not only to handle the cuff but also to handle the connection tube.

Regarding the blood pressure measuring device according to the first aspect of the invention, in the state where the connection tube is housed to as much extent as possible in the connection tube housing by the retraction mechanism, preferably at least a part of the connection tube is located on the outside of the main-unit casing.

With this structure, it is easy to hold the portion of the connection tube that is located on the outside of the main-unit casing so as to draw out the connection tube from the main-unit casing, which ensures convenience and improves the degree of freedom of the direction in which the cuff is housed and the position where the cuff is housed.

Regarding the blood pressure measuring device according to the first aspect of the invention, preferably the main-unit casing has an opening for drawing out the connection tube and, in this case, preferably the connection tube has a stopper portion abutting on a periphery of the opening and thereby preventing the connection tube from being further drawn in into the main-unit casing.

With this structure, the stopper portion abuts on the periphery of the opening to ensure that a part of the connection tube is always positioned on the outside of the main-unit casing. Thus, it is easy to hold the portion of the connection tube that is located on the outside of the main-unit casing so as to draw out the connection tube from the main-unit casing, which ensures convenience and improves the degree of freedom of the direction in which the cuff is housed and the position where the cuff is housed.

Regarding the blood pressure measuring device according to the first aspect of the invention, preferably the connection tube includes a cuff-side tube portion having one end connected to the fluid bag, a main-unit-casing-side tube portion having one end connected to the inflation/deflation mechanism and a connector connecting the other end of the cuff-side tube portion and the other end of the main-unit-casing-side tube portion and, in this case, preferably the stopper portion is formed of the connector.

With this structure, the connector can be used to conveniently form the stopper portion and further, only the cuff-side tube portion that is located closer to the cuff with respect to the connector can be replaced as required. Further, when only the cuff-side tube portion is replaced for example, such an undesired situation can be prevented as the one where the whole connection tube is erroneously drawn into the main-unit casing and thus the connection tube cannot be drawn out from the main-unit casing.

According to a second aspect of the present invention, a blood pressure measuring device includes: a cuff having an inflatable/deflatable fluid bag; a main-unit casing in which an inflation/deflation mechanism inflating/deflating the fluid bag is disposed; a connection tube connecting the fluid bag and the inflation/deflation mechanism; and a retraction mechanism provided at a position on the connection tube and capable of drawing in the connection tube into a connection tube housing provided in the retraction mechanism.

With this structure, in the connection tube housing provided in the retraction mechanism, the connection tube is easily and surely housed. Thus, the blood pressure measuring device can be made superior in housing of the connection tube, particularly in ease of handling of the connection tube. Further, since the connection tube is housed in the retraction mechanism, it can be prevented that the connection tube is bent or twisted for example to be broken.

Regarding the blood pressure measuring device according to the second aspect of the present invention, preferably the retraction mechanism has a wound member on which the connection tube that is drawn in into the connection tube housing is wound.

With this structure, the connection tube in the state of being wound on the wound member is compactly housed in the connection tube housing. Thus, increase in size of the retraction mechanism can be prevented. Further, the relatively simple structure can be used to form the retraction mechanism. Furthermore, since the wound member is used for housing the connection tube, the draw-out/draw-in operation can easily be implemented.

Regarding the blood pressure measuring device according to the second aspect of the present invention, preferably the retraction mechanism has an elastic member coupled to the wound member and, in this case, preferably elastic force of the elastic member rotationally drives the wound member and thereby causes the connection tube to be drawn in into the connection tube housing.

With this structure, the elastic force of the elastic member can be used to draw in the connection tube. Thus, the blood pressure measuring device can be made superior in ease of handling of the connection tube.

Regarding the blood pressure measuring device according to the second aspect of the present invention, preferably the retraction mechanism has a connection tube locking mechanism locking the connection tube against the elastic force of the elastic member.

With this structure, the connection tube in the state of being drawn in/out to an arbitrary extent can be locked by the connection tube locking mechanism. Thus, the blood pressure monitor can be made superior in convenience. Further, in the state where the connection tube is drawn out and the cuff is mounted on a site for taking a measurement, it can be prevented that the elastic force of the elastic member exerts tension on the site for taking a measurement. Thus, the accuracy in measurement can be kept high and the user has to bear no burden.

In accordance with the present invention, the blood pressure measuring device can be provided that is superior in housing of the connection tube for connecting the cuff and the main-unit casing, particularly in ease of handling of the connection tube.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 24A and 24B each show the state where an air tube is drawn in into a retractor unit of the blood pressure monitor, according to the seventh embodiment of the present invention.

DESCRIPTION OF THE PREFERRED EMBODIMENTS

In the following, embodiments of the present invention are described in detail with reference to the drawings. .In the following embodiments, a description is given of an exemplary upper-arm blood pressure monitor which uses the oscillometric method and for which it is intended that the left upper arm is used as a site for taking a measurement.

First Embodiment

Figure 1:
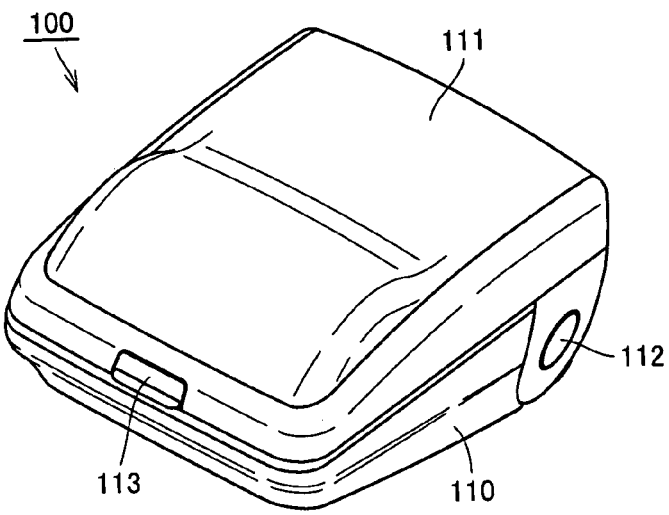
FIG. 1 is a perspective view showing an appearance of a blood pressure monitor and showing the state where an open/close cover is closed, according to a first embodiment of the present invention.
Figure 2:
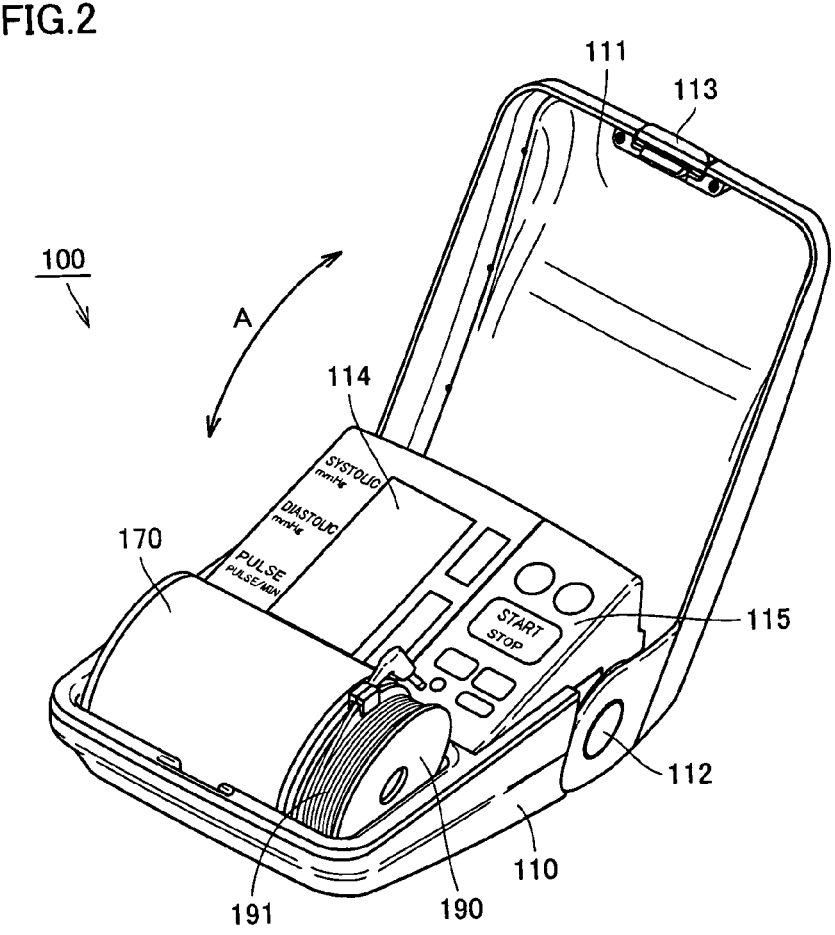
FIG. 2 is a perspective view showing an appearance of the blood pressure monitor and showing the state where the open/close cover is opened, according to the first embodiment of the present invention.
Figure 3:
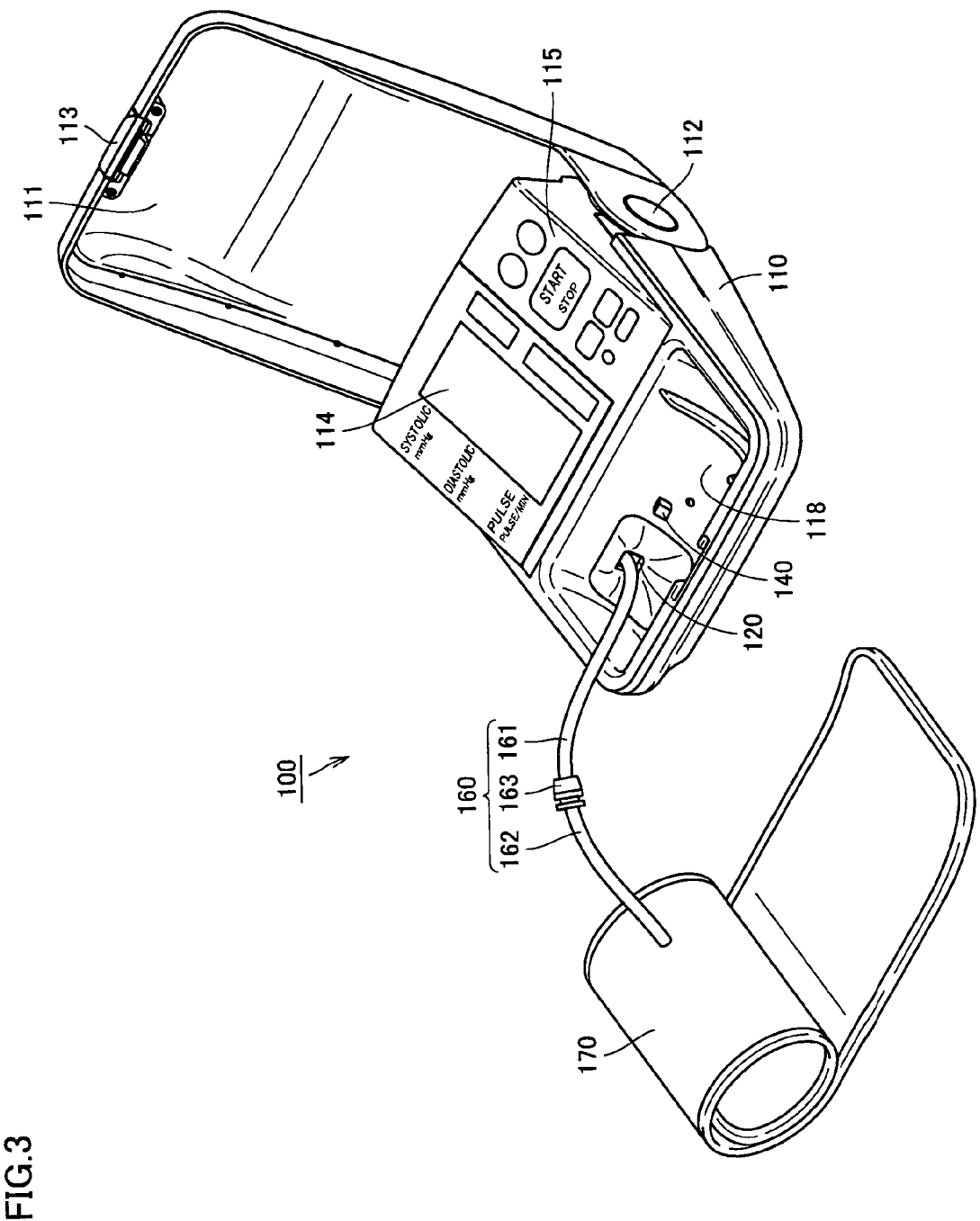
FIG. 3 is a perspective view showing an appearance of the blood pressure monitor and showing the state where the open/close cover is opened and a cuff is taken out of a main-unit casing, according to the first embodiment of the present invention.
Figure 4:
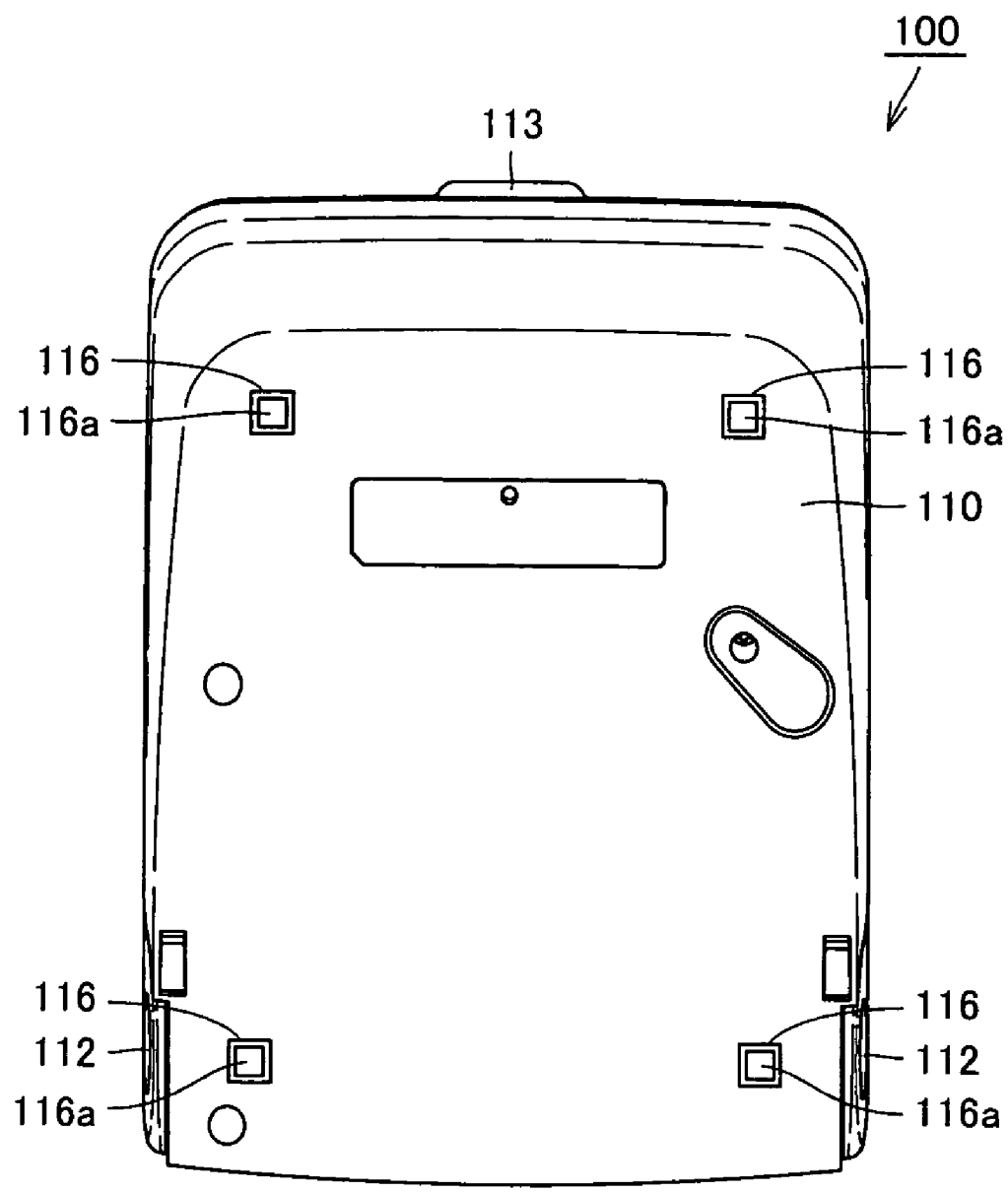
FIG. 4 is a bottom view of the blood pressure monitor according to the first embodiment of the present invention.

FIGS. 1 to 3 are each a perspective view showing an appearance of a blood pressure monitor according to a first embodiment of the present invention. FIG. 1 is a perspective view showing the state where an open/close cover of the blood pressure monitor in the present embodiment is closed, FIG. 2 is a perspective view showing the state where the open/close cover is opened, and FIG. 3 is a perspective view showing the state where a cuff is taken out of a main-unit casing while the open/close cover is opened. FIG. 4 is a bottom view of the blood pressure monitor in the present embodiment. First, with reference to FIGS. 1 to 4, the external structure of blood pressure monitor 100 in the present embodiment is described.

As shown in FIGS. 1 to 3, blood pressure monitor 100 in the present embodiment includes main-unit casing 110 and cuff 170 as its main components. Main-unit casing 110 has open/close cover 111 attached in the manner that the cover in the closed state covers the upper surface of main-unit casing 110. Open/close cover 111 is pivotably coupled to main-unit casing 110 by a hinge 112 provided at a rear portion of main-unit casing 110, and pivots in the direction indicated by the arrow A in FIG. 2. For causing open/close cover 111 to change from the closed state to the opened state, an open/close button 113 provided at a front portion of open/close cover 111 is operated.

At predetermined positions of the upper surface of main-unit casing 110, such components as a display unit 114 and an operation unit 115 are provided. Display unit 114 visibly displays a measured blood pressure value and a measured pulse rate for example by means of numerical values and a graph for example. As display unit 114, a liquid-crystal panel for example is used. At operation unit 115, a power button and a measure/stop button for example are disposed.

In a front portion of main-unit casing 110, a cuff housing 118 is provided. Cuff housing 118 is formed by providing a depressed portion to the upper surface of main-unit casing 110. While open/close cover 111 is in the closed state, open/close cover 111 covers cuff housing 118. In blood pressure monitor 100 as shown, a housing for an AC adapter 191 is provided in parallel with cuff housing 118. In the housing of AC adapter 191, AC adapter 191 wound on a bobbin 190 is housed together with bobbin 190 while blood pressure monitor 100 is not used or a blood pressure value is measured using a DC power supply instead of the AC power supply.

As shown in FIG. 3, cuff 170 and main-unit casing 110 are connected by an air tube 160 serving as a connection tube. Air tube 160 is formed of a flexible tube and is comprised of a main-unit-casing-side air tube 161 serving as a main-unit-casing-side tube portion having one end connected to main-unit casing 110, a cuff-side air tube 162 serving as a cuff-side tube portion having one end connected to cuff 170, and a connector 163 connecting the other end of main-unit-casing-side air tube 161 and the other end of cuff-side air tube 162. The end of air tube 160 that is on the side of cuff 170 is connected to an air bag 171 (see FIG. 5) serving as a fluid bag contained in cuff 170. The end of air tube 160 that is on the side of main-unit casing 110 is connected to an inflation/deflation mechanism 133 (see FIG. 5) provided in main-unit casing 110. Air tube 160 is drawn out from an opening 120 provided in a wall surface of cuff housing 118, to the outside of main-unit casing 110. At cuff housing 118, a lock release button 140 of an air tube locking mechanism which is described hereinlater is provided adjacent to opening 120.

As shown in FIG. 4, at predetermined positions of the bottom surface of main-unit casing 110, a plurality of legs 116 protruding downwardly are provided. Legs 116 are components for stably mounting main-unit casing 110 of blood pressure monitor 100 on such a mount surface as table. A rubber member 116a is attached to the leading end of the legs each. Rubber member 116a is used for preventing, by friction, main-unit casing 110 from moving on the mount surface while air tube 160 is drawn out/drawn in.

Figure 5:
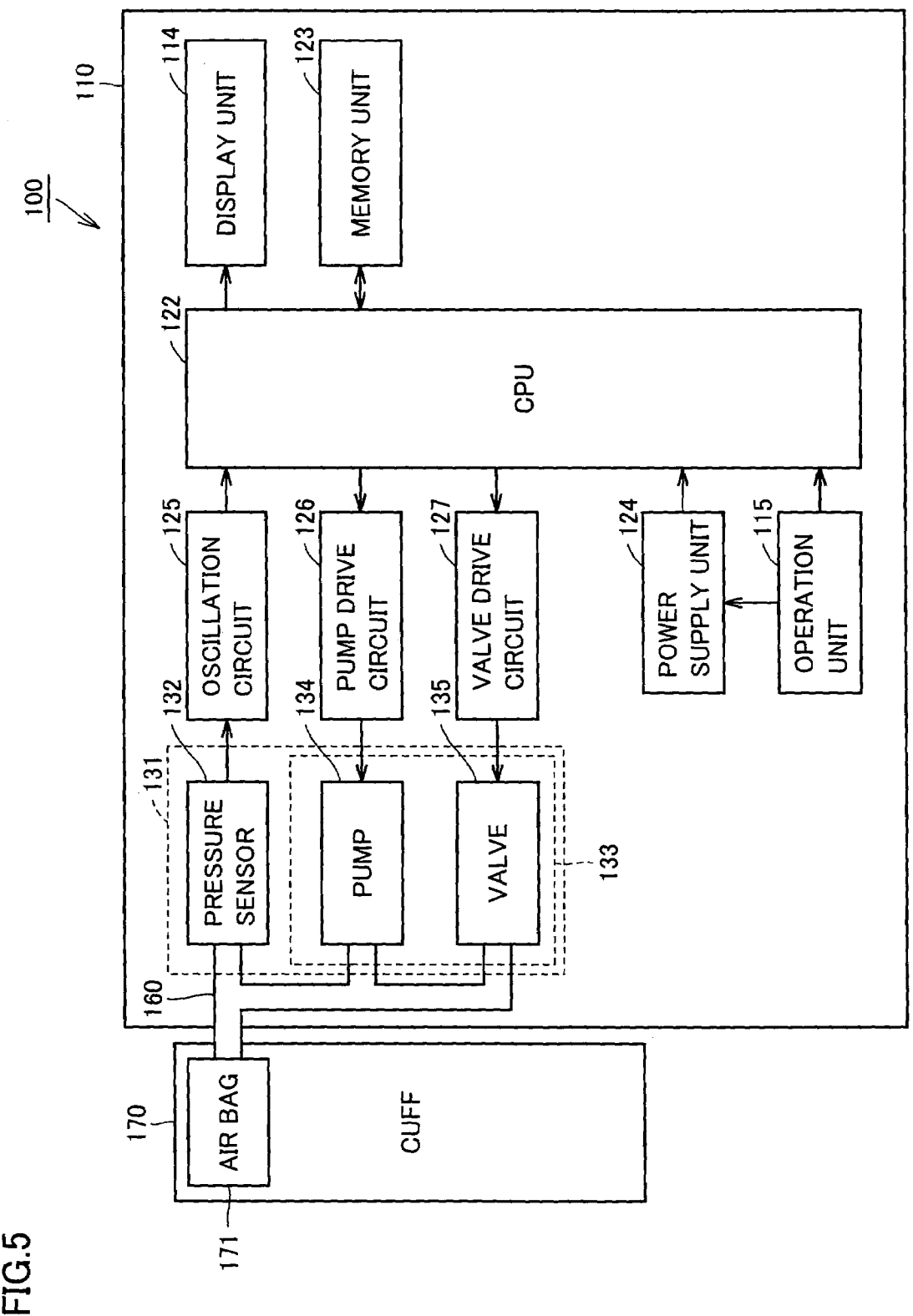
FIG. 5 is a block diagram showing a configuration of the blood pressure monitor according to the first embodiment of the present invention.

FIG. 5 is a block diagram showing a configuration of the blood pressure monitor in the present embodiment. Next, with reference to FIG. 5, a main configuration of blood pressure monitor 100 in the present embodiment is described.

As shown in FIG. 5, in main-unit casing 110, an air system for blood pressure measurement 131 is provided for supplying or discharging air through air tube 160 into or from air bag 171. Air system for blood pressure measurement 131 includes a pressure sensor 132 serving as a pressure detection unit detecting the pressure in air bag 171 and a pump 134 and a valve 135 that are components of an inflation/deflation mechanism 133 for inflating/deflating air bag 171. Further, in main-unit casing 110, an oscillation circuit 125, a pump drive circuit 126 and a valve drive circuit 127 are provided in association with air system for blood pressure measurement 131.

Furthermore, in main-unit casing 110, there are provided a CPU (Central Processing Unit) 122 for centralized control and monitor of the components, a memory unit 123 for storing a program for allowing CPU 122 to perform a predetermined operation as well as various information such as a measured blood pressure value, display unit 114 for displaying various information including the result of measurement of a blood pressure, operation unit 115 operated for entering various instructions for measurement, and a power supply unit 124 for supplying electric power to CPU 122 and the constituent blocks. CPU 122 also serves as a blood pressure value calculation unit for calculating a blood pressure value.

Pressure sensor 132 detects the pressure in air bag 171 (hereinafter referred to as "cuff pressure"), and outputs a signal according to the detected pressure to oscillation circuit 125. Pump 134 supplies air to air bag 171. Valve 135 opens/closes for keeping the pressure in air bag 171 or discharging the air in air bag 171. Oscillation circuit 125 outputs to CPU 122 a signal at an oscillation frequency according to the output value of pressure sensor 132. Pump drive circuit 126 controls drive of pump 134 based on a control signal provided from CPU 122. Valve drive circuit 127 controls opening/closing of valve 135 based on a control signal provided from CPU 122.

Figure 6:
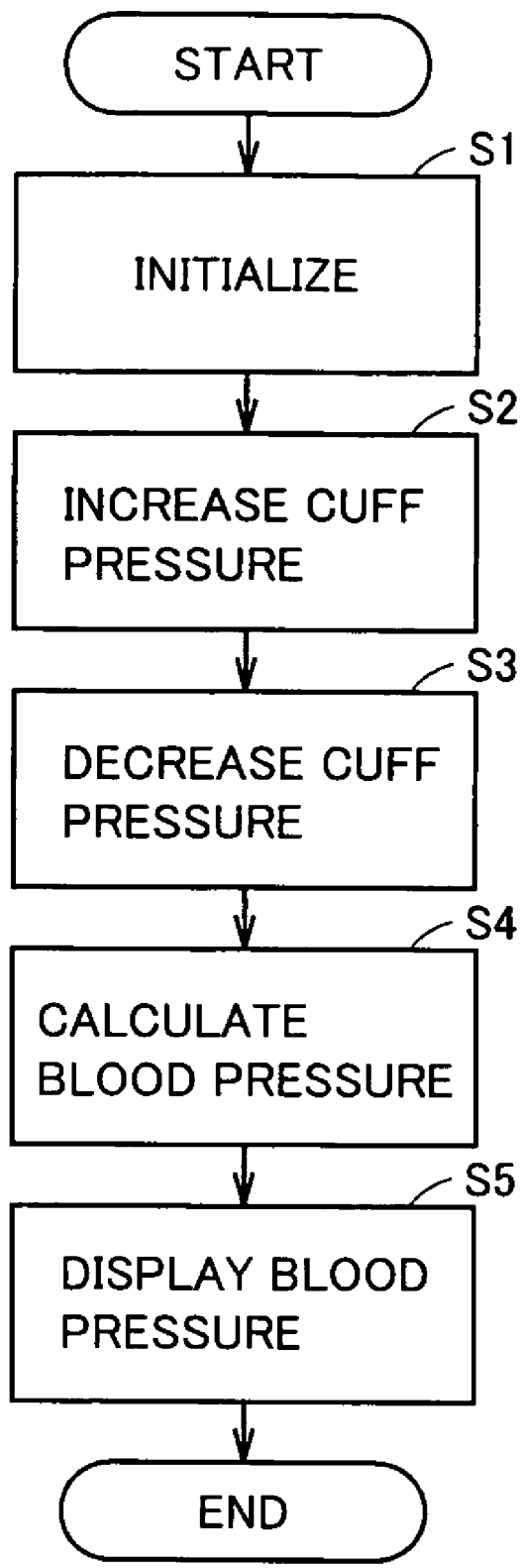
FIG. 6 is a flowchart showing a flow of a process of measuring the blood pressure by the blood pressure monitor according to the first embodiment of the present invention.

FIG. 6 is a flowchart showing a flow of a process of measuring a blood pressure by the blood pressure monitor in the present embodiment. Referring now to FIG. 6, a description is given of the flow of the process of measuring a blood pressure by blood pressure monitor 100 in the present embodiment. A program in accordance with the flowchart is stored in advance in memory unit 123. CPU 122 reads this program from memory unit 123 and executes the program to carry out the process of measuring a blood pressure.

As shown in FIG. 6, a user operates an operation button of operation unit 115 of blood pressure monitor 100 to turn on the power, and accordingly blood pressure monitor 100 is initialized (step S1). Then, when the state where a measurement can be taken is reached, CPU 122 starts driving pump 134 to gradually increase the cuff pressure of air bag 171 (step S2). In the process of gradually pressurizing, when the cuff pressure reaches a predetermined level for measuring the blood pressure, CPU 122 stops pump 134 and then gradually opens valve 135 which has been closed, so as to gradually discharge the air in air bag 171 and gradually decrease the cuff pressure (step S3). Regarding blood pressure monitor 100 in the present embodiment, the blood pressure value is measured in the process of decreasing the cuff pressure at a very low rate.

Subsequently, CPU 122 calculates the blood pressure value (systolic pressure, diastolic pressure) through the known procedure (step S4). Specifically, in the stage where the cuff pressure is gradually decreased, CPU 122 extracts pulse-wave information based on the oscillation frequency obtained from oscillation circuit 125. Then, from the extracted pulse-wave information, the blood pressure value is calculated. As the blood pressure value is calculated in step S4, the calculated blood pressure value is displayed on display unit 114 (step S5). While the above-described method of taking a measurement is based on the so-called pressure-decreased stage measurement method detecting pulse waves while the pressure of the air bag is decreased, it would clearly be seen that the so-called pressure-increased stage measurement method detecting pulse waves while the pressure of the air bag is increased may be used.

Figure 7:
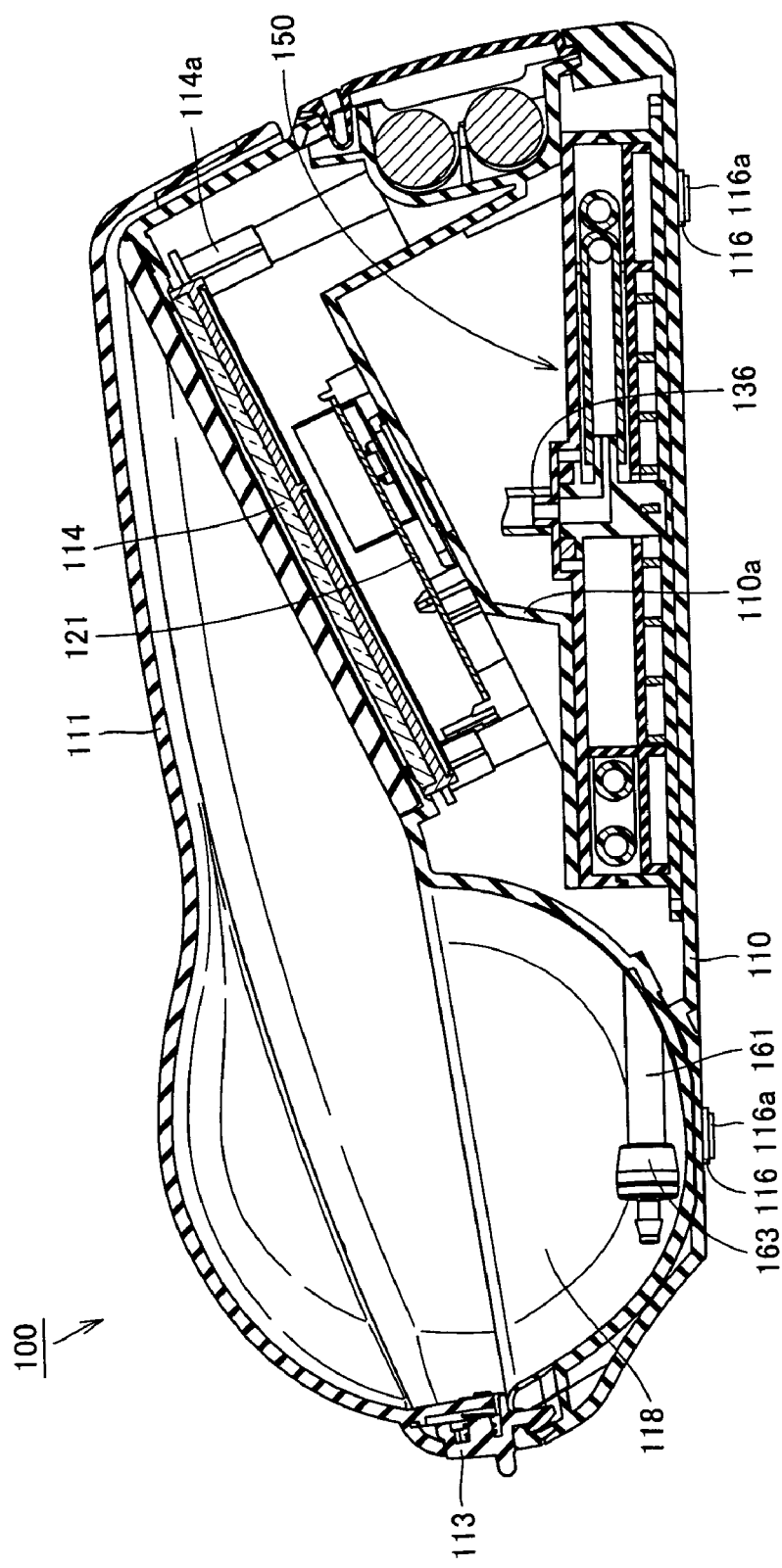
FIG. 7 is a schematic cross-sectional view showing an internal structure of the blood pressure monitor according to the first embodiment of the present invention.

FIG. 7 is a schematic cross-sectional view showing an internal structure of the blood pressure monitor in the present embodiment. In FIG. 7, the cuff and the cuff-side air tube are not shown. Referring now to FIG. 7, the internal structure of blood pressure monitor 100 in the present embodiment is described.

As shown in FIG. 7, in blood pressure monitor 100 of the present embodiment, a partition 110a is provided in main-unit casing 110. Partition 110a divides the space within main-unit casing 110 into an upper space and a lower space. In the upper space, there is provided a circuit board 121 where such components as CPU 122, memory unit 123, oscillation circuit 125, pump drive circuit 126 and valve drive circuit 127 as described above are provided. Further, in the upper space, such a component as a display support frame 114a for supporting display unit 114 formed of liquid crystal display is also provided.

In the lower space, such components as a retractor unit 150 serving as a retraction (draw-in) mechanism and air system for blood pressure measurement 131 described above are provided. Retractor unit 150 is formed of a disk-shaped assembly having therein an air tube housing 155A (see FIGS. 8A, 8B, 9A and 9B) serving as a connection tube housing, and the retractor unit is disposed horizontally in main-unit casing 110 in the manner that the main surface of the retractor unit is in parallel with the bottom surface of main-unit casing 110. Retractor unit 150 is connected to air system for blood pressure measurement 131 by an intermediate air tube 136 and accordingly air tube 160 is connected via retractor unit 150 and intermediate air tube 136 to air system for blood pressure measurement 131 including inflation/deflation mechanism 133.

Figure 8A:
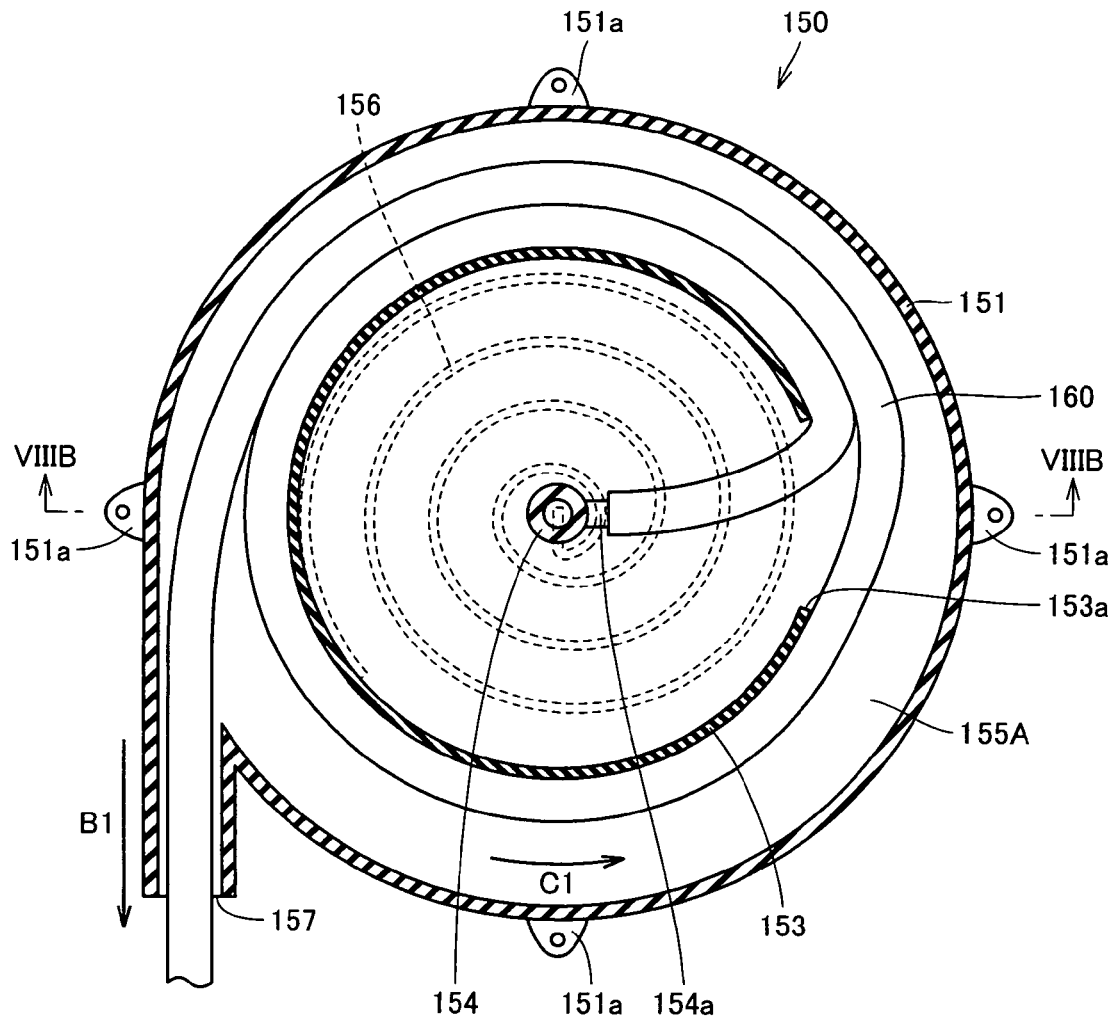
FIG. 8A is a schematic cross-sectional view showing the state where an air tube is drawn in into a retractor unit of the blood pressure monitor according to the first embodiment of the present invention.
Figure 8B:
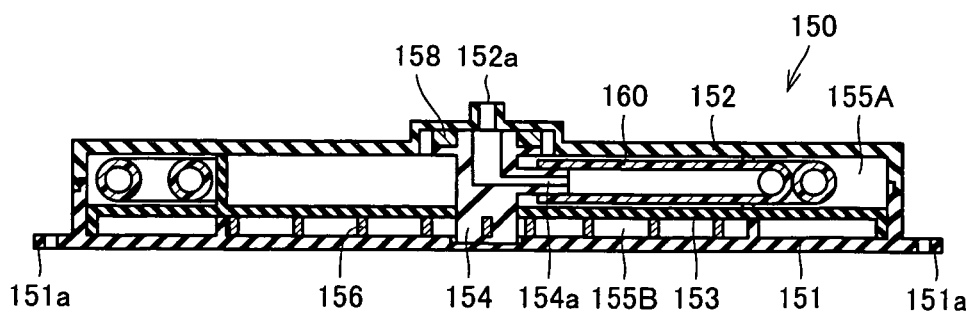
FIG. 8B is a schematic cross-sectional view along the line VIIIB-VIIIB shown in FIG. 8A.
Figure 9A:
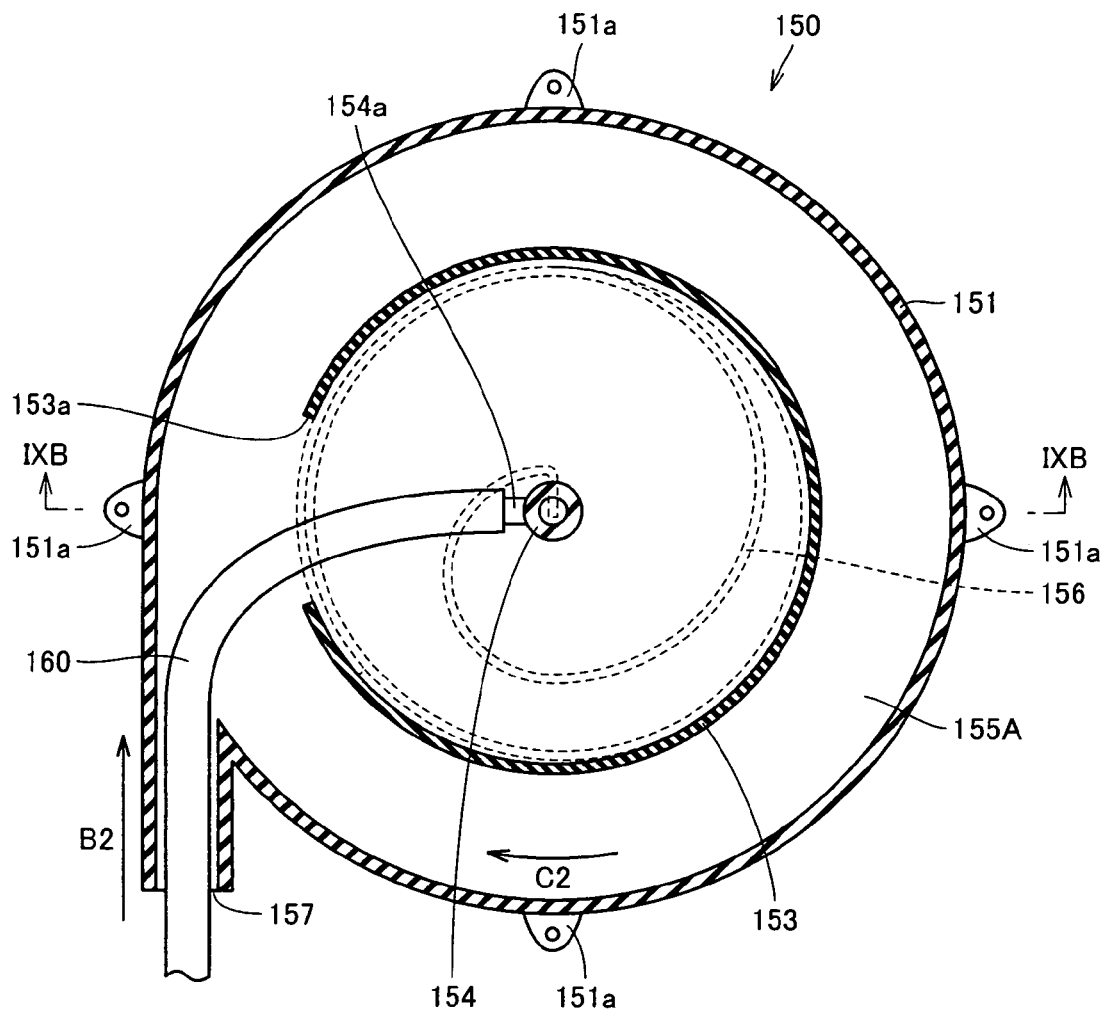
FIG. 9A is a schematic cross-sectional view showing the state where the air tube is drawn out from the retractor unit of the blood pressure monitor according to the first embodiment of the present invention.
Figure 9B:
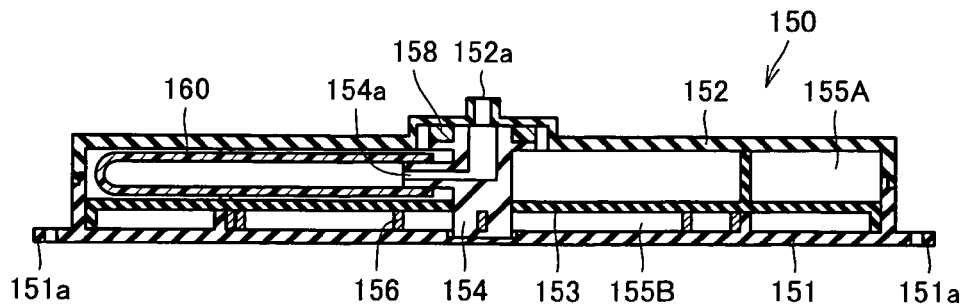
FIG. 9B is a schematic cross-sectional view along the line IXB-IXB shown in FIG. 9A.
Figure 10A:
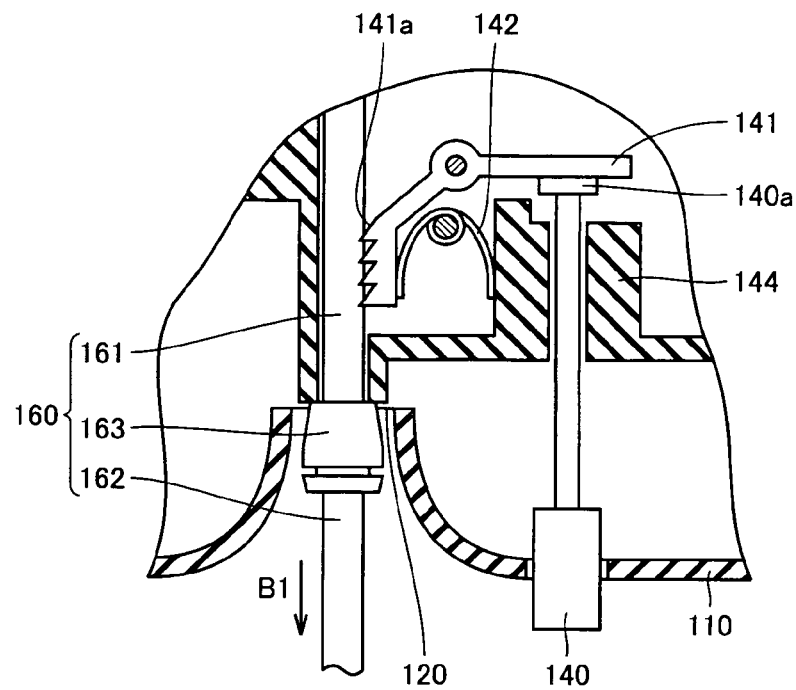
FIGS. 10A and 10B each show an air tube locking structure of the blood pressure monitor according to the first embodiment of the present invention.
Figure 10B:
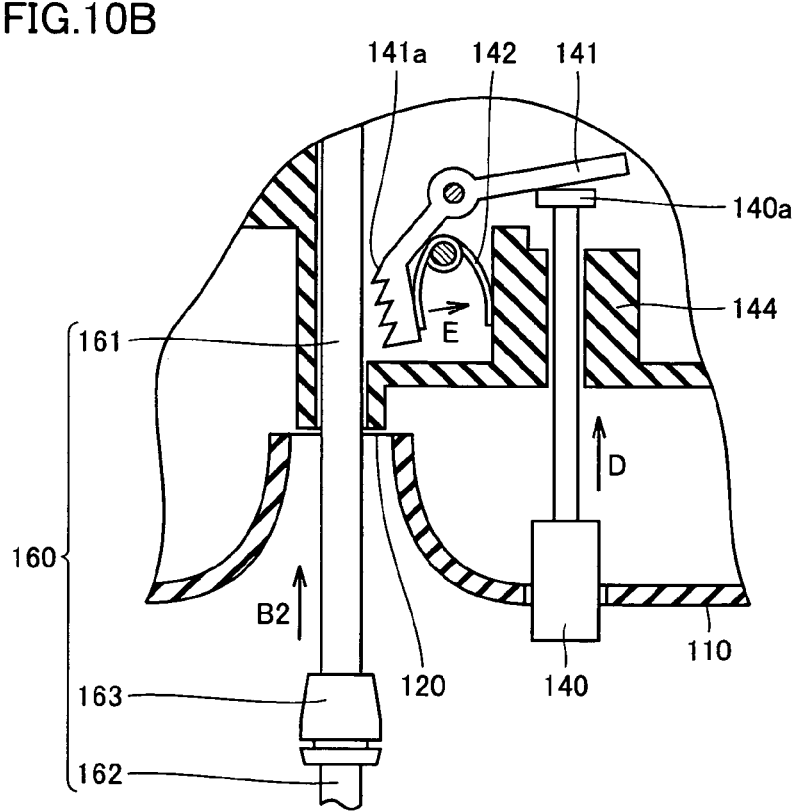

FIGS. 8A, 8B, 9A and 9B illustrate the structure of the retractor unit of the blood pressure monitor and an operation of drawing out/drawing in (retracting) the air tube, according to the present embodiment. FIGS. 8A and 8B show the case where the air tube is drawn in into the retractor unit. FIG. 8A is a cross-sectional view along a horizontal plane of the retractor unit, and FIG. 8B is a cross-sectional view along the line VIIIB-VIIIB of the retractor unit shown in FIG. 8A. FIGS. 9A and 9B show the case where the air tube is drawn out from the retractor unit. FIG. 9A is a cross-sectional view along a horizontal plane of the retractor unit, and FIG. 9B is a cross-sectional view along the line IXB-IXB of the retractor unit shown in FIG. 9A. FIGS. 10A and 10B illustrate the structure of the air tube locking mechanism of the blood pressure monitor in the present embodiment and an operation of drawing out/drawing in the air tube. FIG. 10A is a cross-sectional view showing the case where the air tube is locked, and FIG. 10B is a cross-sectional view showing the case where the lock of the air tube is released.

Referring first to FIGS. 8A, 8B, 9A and 9B, the structure of retractor unit 150 is described. As shown in FIGS. 8A, 8B, 9A and 9B, retractor unit 150 is formed by assembling a lower case 151 and an upper case 152 constituting a shell, a bobbin 153 serving as a wound member, a shaft tube 154, and a spiral spring 156 serving as an elastic member.

Lower case 151 is formed of a bottomed cylindrical member having a disk-shaped bottom surface, and has, on its outer periphery, a seizing portion 151a for fixing retractor unit 150 with respect to main-unit casing 110. Upper case 152 is formed of a bottomed cylindrical member having a disk-shaped bottom plate and has its central portion provided with a connection opening 152a. Connection opening 152a is a portion where intermediate air tube 136 is connected in the state where retractor unit 150 is mounted on main-unit casing 110. Lower case 151 and upper case 152 are attached with respective opening surfaces facing each other and accordingly a space is formed inside the cases.

Bobbin 153 is rotatably provided in the aforementioned space formed by lower case 151 and upper case 152 to divide the space into an upper space and a lower space. The space defined by upper case 152 and bobbin 153 is air tube housing 155A in which air tube 160 is housed. The space defined by lower case 151 and bobbin 153 is a spiral spring housing 155B in which spiral spring 156 is housed.

Shaft tube 154 is fixed at a central portion of bobbin 153 and rotates together with bobbin 153. At an upper portion of shaft tube 154, a channel is provided having one end communicating with connection opening 152a provided in upper case 152 as described above. The other end of the channel communicates with a connection opening 154a formed to outwardly protrude from the peripheral surface of shaft tube 154. To this connection opening 154a, air tube 160 is connected. Between upper case 152 and shaft tube 154, such a seal member 158 as O ring is provided for ensuring airtightness.

Air tube 160 having one end attached to connection opening 154a of shaft tube 154 is drawn out toward the outside of bobbin 153 from a draw-out opening 153a provided in the peripheral surface of bobbin 153, and the drawn-out portion is wound on the peripheral surface of bobbin 153 in air tube housing 155A. The other end of air tube 160 is drawn out to the outside of retractor unit 150 from an air-tube draw-out opening 157 provided at a predetermined position of the outer peripheral portion of lower case 151 and upper case 152.

Spiral spring 156 is housed in spiral spring housing 155B, has one end fixed to a lower portion of shaft tube 154 and has the other end fixed at a predetermined position of lower case 151.

With reference now to FIGS. 10A and 10B, a description is given of the structure of the air tube locking mechanism serving as the connection tube locking mechanism for fixing the length of the portion of air tube 160 that is drawn out from main-unit casing 110 to an arbitrary length. The air tube locking mechanism is provided at a wall of main-unit casing 110 that is in a portion located in front of retractor unit 150. As shown in FIGS. 10A and 10B, the air tube locking mechanism is comprised of a lock release button 140, a lock member 141 and a spring 142.

Lock release button 140 is provided at a wall surface that defines cuff housing 118 of main-unit casing 110. Lock member 141 is rotatably supported at its substantially central portion. At a portion closer to one end of lock member 141, a lock portion 141a is provided for locking air tube 160 to prevent the air tube from moving. On a portion closer to the other end of lock member 141, a rear end 140a of lock release button 140 abuts. Spring 142 is provided between the portion where lock portion 141a of lock member 141 is provided and an inner frame body 144 provided inside main-unit casing 110.

Air tube 160 is, as shown in FIG. 10A, locked by a biasing force of spring 142 so that the air tube cannot move. Specifically, lock portion 141a of lock member 141 is pressed against air tube 160 by the biasing force of spring 142, and thus air tube 160 is locked at an arbitrary position by friction. In the case where the locking of air tube 160 is to be released, as shown in FIG. 10B, lock release button 140 is pressed backwardly (in the direction indicated by the arrow D in the drawing) so as to rotate lock member 141 in the direction indicated by the arrow E against the biasing force of spring 142, and thereby release the abutment of lock member 141a on air tube 150.

Next, a description is given of the operation of drawing out/drawing in air tube 160. As shown in FIGS. 8A and 8B, in the state where air tube 160 is housed in air tube housing 155A, air tube 160 wound on bobbin 153 is held in this state in air tube housing 155A. In this state, no external force is applied to spiral spring 156 and thus spiral spring 156 is substantially free. When air tube 160 is to be drawn out, the user holds a portion of air tube 160 that is drawn out and located on the outside of main-unit casing 110, and pulls air tube 160. Then, air tube 160 is pulled in the direction indicated by the arrow B1 in the drawing and accordingly bobbin 153 is rotated in the direction indicated by the arrow C1. Thus, air tube 160 is fed from air-tube draw-out opening 157 to the outside of retractor unit 150. Lock portion 141a of lock member 141 is shaped as shown in FIG. 10A and accordingly air tube 160 can be drawn out without particularly operating lock release button 140.

As bobbin 153 is rotated, shaft tube 154 is also rotated in the direction indicated by the arrow C1 in FIG. 8A. Accordingly, to spiral tube 156 having one end fixed to shaft tube 154, a force is also applied in the rotational direction and this force causes spiral spring 156 to elastically deform. With the elastic deformation, a resilient force is generated at spiral spring 156. However, the presence of the locking mechanism of air tube 160 as described above allows air tube 160 to be locked in the state where air tube 160 is drawn out by a predetermined extent from main-unit casing 110.

As shown in FIGS. 9A and 9B, in the state where air tube 160 is drawn out from air tube housing 155A to as much extent as possible, air tube 160 is not wound on bobbin 153 and the above-described resilient force is generated at spiral spring 156. In this state, as the user presses down lock release button 140 as shown in FIG. 10B, the resilient force that spiral spring 156 has causes shaft tube 154 to be rotated in the direction indicated by the arrow C2 in the drawing and accordingly bobbin 153 is rotated in the direction indicated by the arrow C2. As bobbin 153 is rotated, air tube 160 is drawn in via air-tube draw-out opening 157 into retractor unit 150 in the direction indicated by the arrow B2 in the drawing, and is wound by means of bobbin 153.

Figure 11:
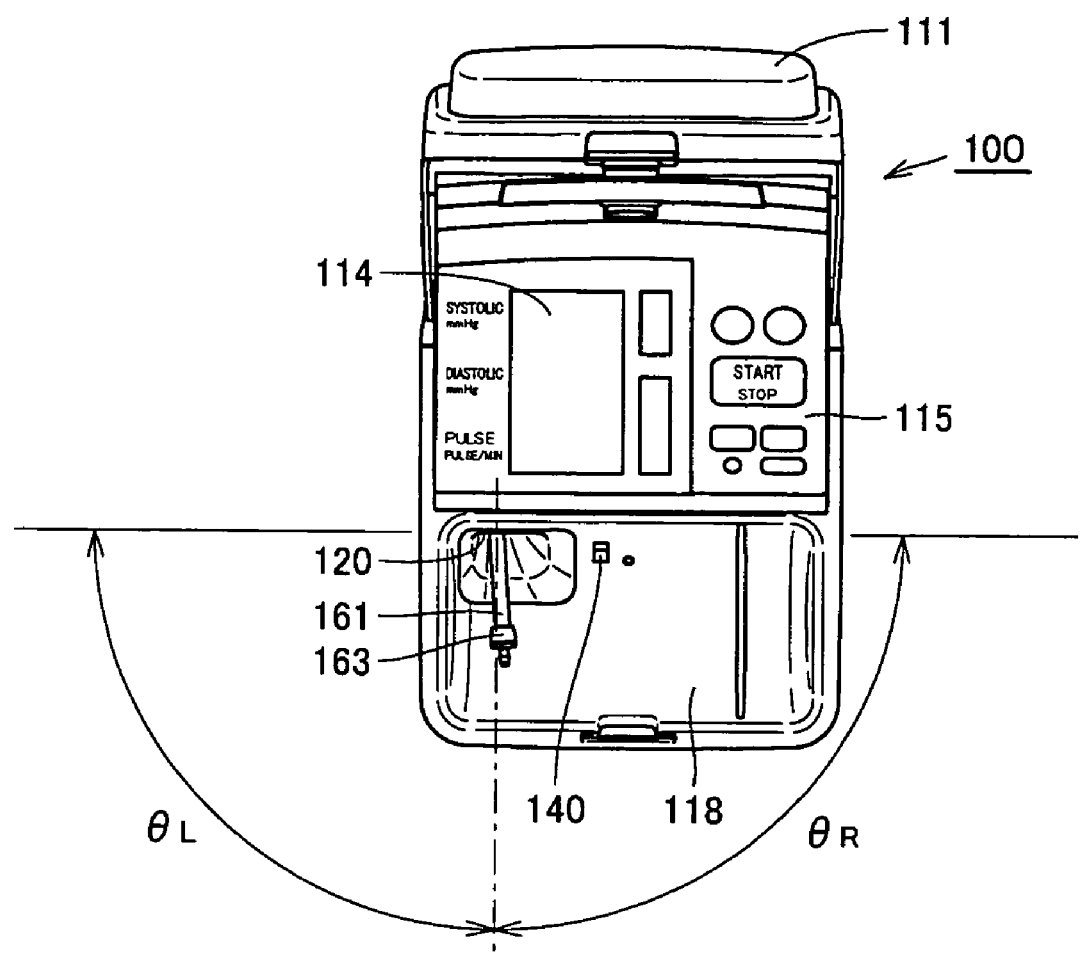
FIG. 11 is a top view of the blood pressure monitor for illustrating a position where an opening is formed that is provided in the main-unit casing of the blood pressure monitor for drawing out the air tube, according to the first embodiment of the present invention.

FIG. 11 is a top view of the blood pressure monitor in the present embodiment, for illustrating a position where an opening provided in the main-unit casing is to be formed for drawing out the air tube. As shown in FIG. 11, in blood pressure monitor 100 in the present embodiment, cuff housing 118 is provided in a front portion of main-unit casing 110 and, in this cuff housing 118, opening 120 for drawing out air tube 160 from main-unit casing 110 is provided. This structure allows opening 120 for drawing out air tube 160 to be provided in the front portion of main-unit casing 110, which facilitates handling of air tube 160.

In blood pressure monitor 100 in the present embodiment, opening 120 is provided in a left-side portion of the wall surface defining cuff housing 118. Opening 120 opens in the frontward direction of main-unit casing 110, and air tube 160 is drawn out in the frontward direction of main-unit casing 110. For blood pressure monitor 100 in the present embodiment, it is intended that the cuff is mounted on the left upper arm. Thus, the fact that opening 120 is provided on the left-side portion of main-unit casing 110 means that air tube 160 is not an obstacle, which is convenient for the user when the cuff is mounted for example. Further, in the case where the cuff is mounted on the left upper arm, the air tube may be drawn out to a relatively small extent and accordingly the air tube may be made short and retractor unit 150 can be reduced in size. In the case where it is intended that the cuff of the blood pressure monitor is mounted on the right upper arm, the opening is preferably provided on the opposite side, namely a right-side portion of the main-unit casing. In the case where it is intended that the cuff is mounted on any one of the right and left upper arms, the opening may be provided at a central portion of the main-unit casing.

Furthermore, preferably air tube 160 is drawn out in the frontward direction with respect to main-unit casing 110 as described above. More specifically, as shown in FIG. 11, preferably air tube 160 is drawn out in the range of angles indicated by θL and θR as seen from above main-unit casing 110. Usually, the user who are using blood pressure monitor 100 is located on the front side of main-unit casing 110. Therefore, by allowing air tube 160 to be drawn out in the above-described direction, the blood pressure monitor can be made superior in ease of use.

Moreover, as shown in FIG. 11, in the state where air tube 160 is drawn in into main-unit casing 110 to as much extent as possible, preferably a part of air tube 160 is located on the outside of the main-unit casing. Blood pressure monitor 100 in the present embodiment is structured in the manner that connector 163 of air tube 160 is located on the outside of main-unit casing 100 in the state where air tube 160 is drawn in into main-unit casing 110 to as much extent as possible. Specifically, the outer shape of connector 163 is formed to be larger than opening 120 and, as connector 163 abuts on the periphery of opening 120, the air tube is not further drawn in into main-unit casing 110. Namely, connector 163 is structured as a stopper portion. With this structure, the drawn-out part of air tube 160 can be held to be pulled out from main-unit casing 110 easily. Thus, the convenience is ensured and the degree of freedom in direction of the cuff while it is housed or position where the cuff is housed is improved.

Figure 12A:
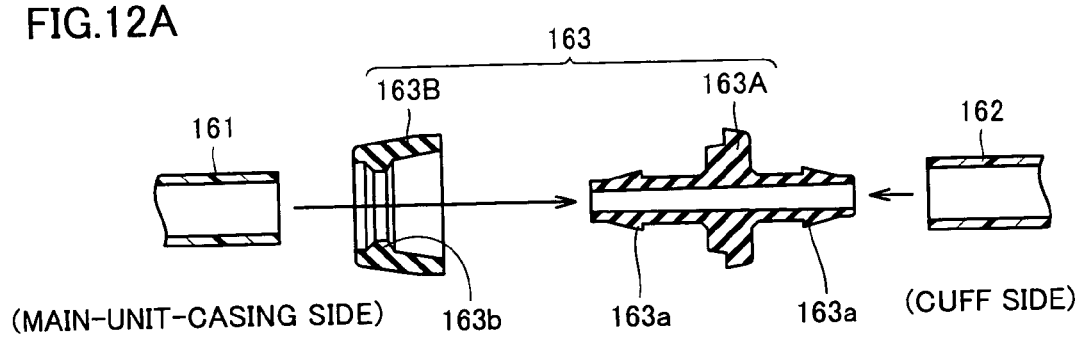
FIGS. 12A to 12C each illustrate a connection structure for the air tube of the blood pressure monitor according to the first embodiment of the present invention.
Figure 12B:
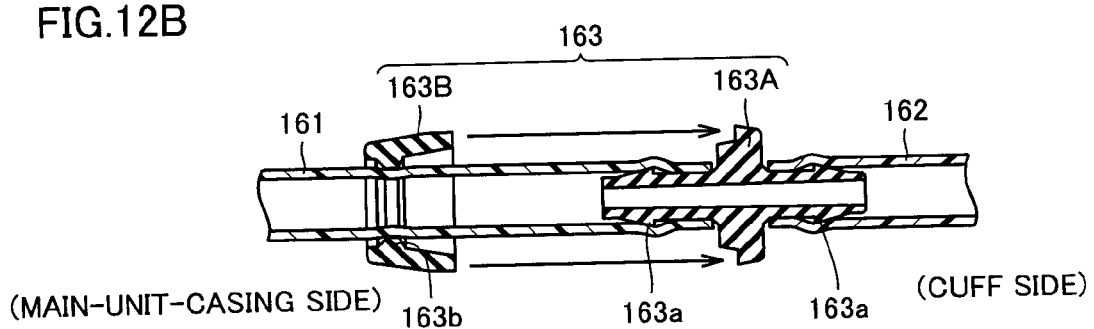
Figure 12C:
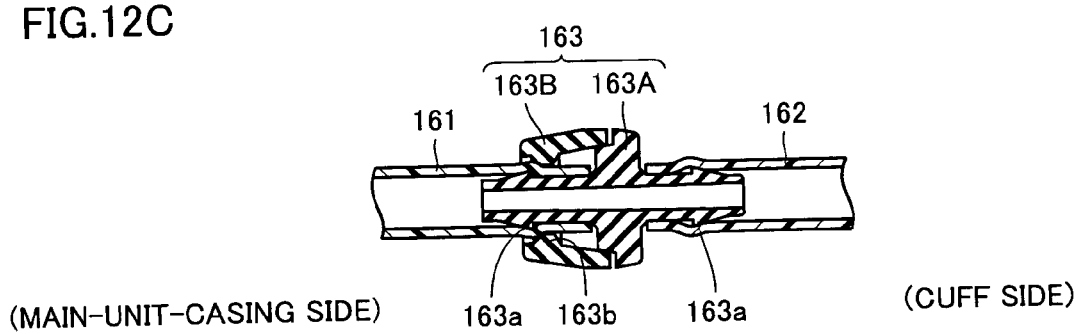

FIGS. 12A to 12C illustrate a connection structure of the air tube of the blood pressure monitor in the present embodiment. For blood pressure monitor 100 in the present embodiment, in order that the cuff can be replaced as required, air tube 160 is divided into main-unit-casing-side air tube 161 and cuff-side air tube 162 and these are connected by connector 163. Connector 163 is comprised of two members that are a first connector member 163A and a second connector member 163B.

First connector member 163A has its two opposing ends provided with respective connection openings to which air tubes 161 and 162 are connected respectively. On respective peripheries of the connection openings, projections 163a are respectively provided for preventing air tubes 161 and 162 from being disconnected. Cuff-side air tube 162 is connected to connector 163 by means of this projection 163a only so that it can relatively easily be inserted/removed when the cuff is replaced. In contrast, main-unit-casing-side air tube 161 is firmly fixed to first connector member 163 A by means of second connector unit 163B since it is unlikely that main-unit-casing-side air tube 161 has to be detached from connector 163. Specifically, on the inside of second connector member 163B, a projection 163b is provided for preventing disconnection, and this projection 163b and projection 163a hold therebetween a portion near the leading end of main-unit-casing-side air tube 161 so as to prevent connector 163 from dropping off main-unit-casing-side air tube 16a.

When air tubes 161 and 162 are connected by means of connector 163, as shown in FIG. 12A, second connector member 163B is first fit on main-unit-casing-side air tube 161 and, on respective connection openings of first connector member 163A, respective leading ends of main-unit-casing-side air tube 161 and cuff-side air tube 162 are fit. Subsequently, as shown in FIG. 12B, second connector member 163B fit in advance on main-unit-casing-side air tube 161 is slid to be fixed to first connector member 163A. At this time, projection 163b provided at second connector member 163 goes over projection 163a provided at first connector member 163A. In this way, the connection structure as shown in FIG. 12C can be obtained.

As described hereinabove, blood pressure monitor 100 in the present embodiment uses retractor unit 150 to easily and surely house air tube 160 in air tube housing 155A provided in retractor unit 150, and thus is superior in housing of air tube 160, particularly superior in ease of handling of air tube 160. Further, since air tube 160 is housed in main-unit casing 110 by means of retractor unit 150, it can be prevented that air tube 160 is bent or twisted for example to be broken.

Furthermore, since air tube 160 wound on bobbin 153 is housed compactly in air-tube housing 155A, increase in size of retractor unit 150 can be prevented and retractor unit 150 can be structured with the relatively simple structure. In addition, since bobbin 153 is used to house air tube 160, the draw-out/draw-in operation can easily be implemented.

Moreover, since the elastic force of spiral spring 156 is used to allow air tube 160 to be drawn in (retracted), the blood pressure monitor can be made superior in ease of handling of air tube 160. Further, since air tube 160 can be locked in the state where air tube 160 is drawn out of main-unit casing 100 to an arbitrary extent, the blood pressure monitor can be made superior in terms of convenience. Furthermore, in the state where air tube 160 is drawn out and the cuff is mounted on the left upper arm, it is prevented by the air tube locking mechanism that the resilient force of spiral spring 156 is applied to the upper arm. Thus, the accuracy in measurement can be kept high and the user has to bear no burden.

Second Embodiment

Figure 13:
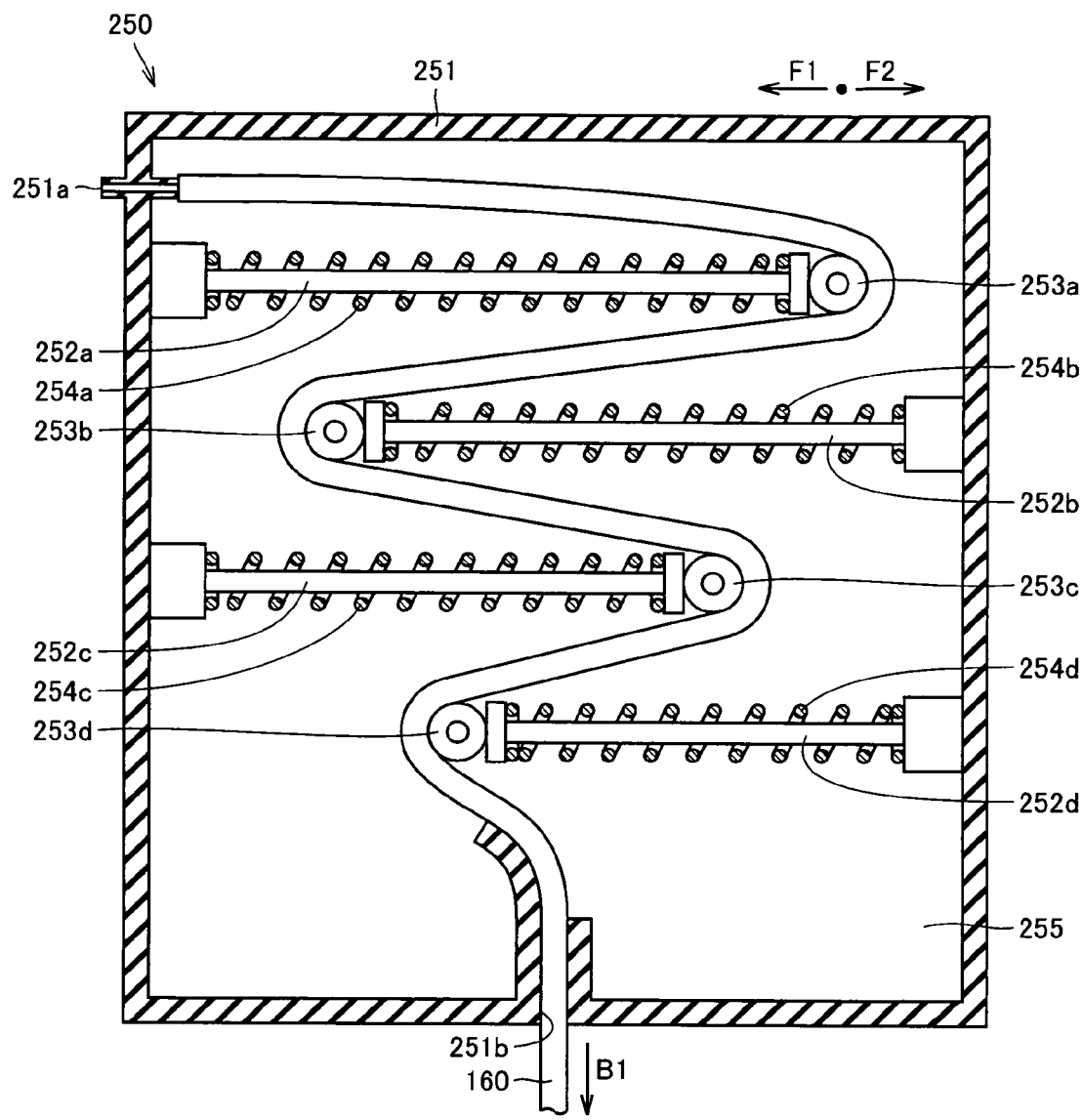
FIG. 13 shows the state where an air tube is drawn in into a retractor unit of a blood pressure monitor according to a second embodiment of the present invention.
Figure 14:
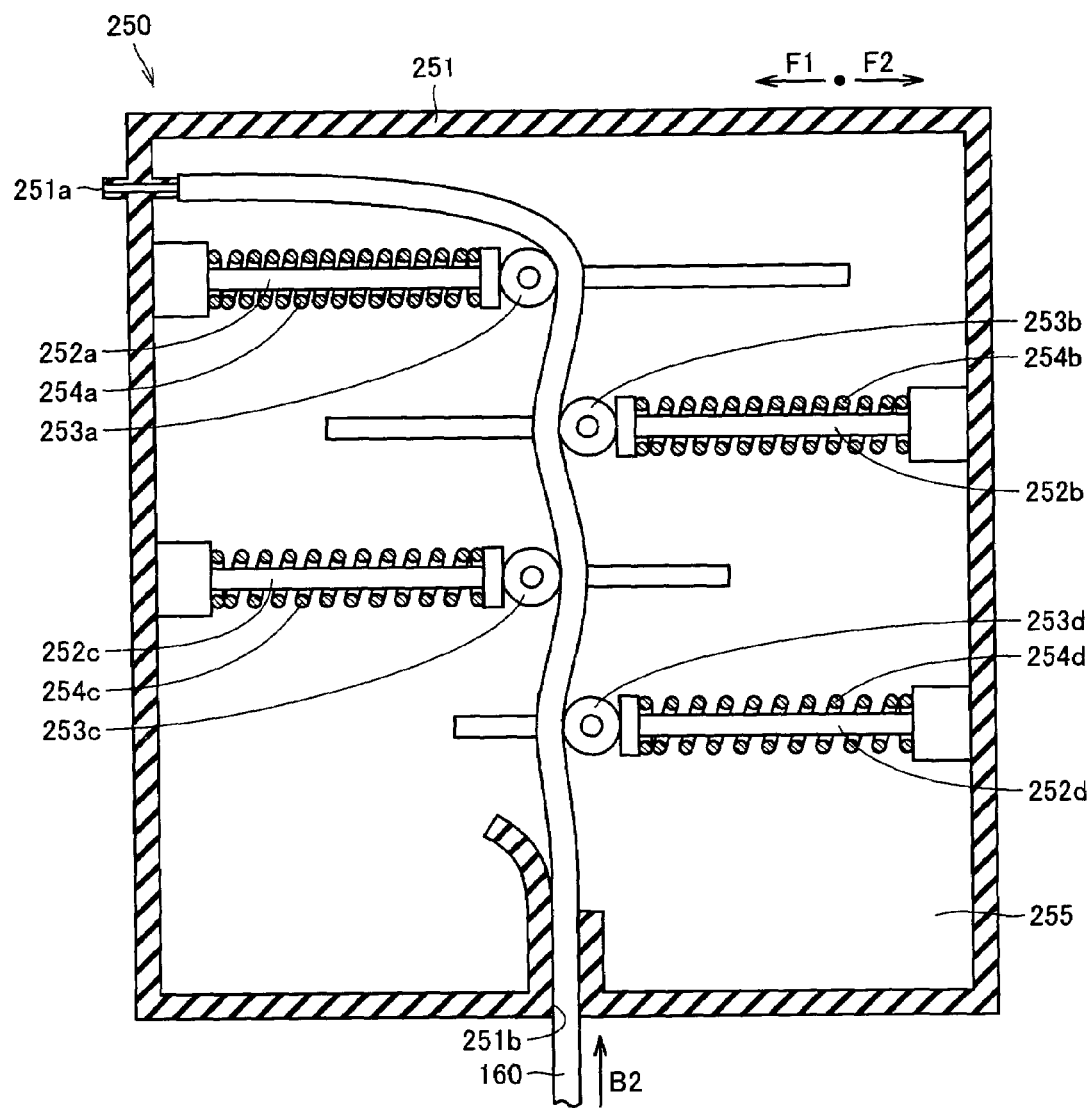
FIG. 14 shows the state where an air tube is drawn out from a retractor unit of the blood pressure monitor according to the second embodiment of the present invention.

FIGS. 13 and 14 illustrate a structure of a retractor unit of a blood pressure monitor as well as an operation of drawing out/drawing in an air tube, according to a second embodiment of the present invention. FIG. 13 shows the case where the air tube is drawn in into the retractor unit and FIG. 14 shows the case where the air tube is drawn out from the retractor unit. The blood pressure monitor in the present embodiment is identical to the blood pressure monitor in the first embodiment except for the structure of the retractor unit, and the description of components except for those relevant to the retractor unit is not repeated here.

Referring first to FIGS. 13 and 14, the structure of retractor unit 250 is described. As shown in FIGS. 13 and 14, retractor unit 250 is formed by assembling a case 251 forming a shell, as well as guide shafts 252a to 252d, guide rolls 253a to 253d and coil springs 254a to 254d that serve as components of a housing mechanism housing air tube 160 in a meandering state.

Case 251 is formed of a rectangular box and has its inner space corresponding to an air tube housing 255. In air tube housing 255 that is the inner space of case 251, guide shafts 252a to 252d, guide rolls 253a to 253d and coil springs 254a to 254d are provided. At a predetermined position of a rear portion of case 251, a connection opening 251a is provided where air tube 160 is connected oh the inside of case 251. To a portion of connection opening 251a that is located on the outside of case 251, an intermediate air tube 136 is connected. Further, at a predetermined position of a front portion of case 251, an air-tube draw-out opening 251b is provided from which air tube 160 is drawn out.

One of guide shafts 252a to 252d, corresponding one of guide rolls 253a to 253d and corresponding one of coil springs 254a to 254d are combined to constitute one of four housing mechanisms. The four housing mechanisms are mounted, on the inside of case 251, alternately on the right and left walls. Housing mechanisms are structured respectively in the manner that guide rolls 253a to 253d are movably attached to respective guide shafts 252a to 252d provided to erect from the wall surface of case 251, and coil springs 254a to 254d are fitted on respective guide shafts 252a to 252d so as to bias guide rolls 253a to 253d in the direction toward the leading ends of guide shafts 252a to 252d. Air tube 160 is passed to extend between these housing mechanisms and thus air tube 160 extending in meandering state is housed in case 251.

Next, the operation of drawing out/drawing in air tube 160 is described. As shown in FIG. 13, in the state where air tube 160 is housed in air tube housing 255, air tube 160 is housed in meandering state by means of the housing mechanisms. In this state, no external force is applied to coil springs 254a to 254d and coil springs 254a to 254d are substantially free. When air tube 160 is to be drawn out, the user holds a portion of air tube 160 that is drawn out to be located on the outside of main-unit casing 110, and pulls air tube 160. Thus, air tube 160 is pulled in the direction indicated by the arrow B1 in the drawing and accordingly guide rolls 253a to 253d are pushed down in the direction indicated by the arrow F1 or F1 in the drawing, and air tube 160 is fed from air-tube draw-out opening 251b to the outside of retractor unit 250. As guide rolls 253a to 253d are moved, coil springs 254a to 254d are compressed. As this elastic deformation occurs, a resilient force is generated at coil springs 254a to 254d. However, an air tube locking mechanism is separately provided to main-unit casing 110 of blood pressure monitor 100, so that the air tube is locked in the state where the air tube is drawn out from retractor unit 250 to a desired extent.

As shown in FIG. 14, in the state where air tube 160 is drawn out to as much extent as possible from air tube housing 255, air tube 160 extends substantially linearly and the above-described resilient force is generated at coil springs 254a to 254d. In this state, as the user releases the locking of air tube 160 effected by the air tube locking mechanism provided to blood pressure monitor 100, the resilient force of coil springs 254a to 254d causes guide rolls 253a to 253d on guide shafts 252a to 252d to move toward the leading ends of guide shafts 252a to 252d in the direction indicated by the arrow F1 or F2 in the drawing. Thus, air tube 160 is caused to extend in meandering state. Accordingly, a most part of air tube 160 is housed in air tube housing 255.

In the case where retractor unit 250 as described above is provided as well, air tube 160 can be housed compactly in meandering state in air tube housing 255. Thus, retractor unit 250 can be prevented from being increased in size, and retractor unit 250 can be formed to have the relatively simple structure. Accordingly, effects similar to those of the first embodiment can be obtained and the blood pressure monitor can be made superior in housing of air tube 160.

Regarding blood pressure monitor 100 in the present embodiment, the description is given hereinabove of a case as an example where the blood pressure monitor is structured in the manner that, as the user holds and pulls air tube 160, air tube 160 is fed to the outside of main-unit casing 110. Alternatively, such a drive unit as motor may be provided to retractor unit 250 and this motor may be used to drive guide rolls 253a to 253d and move the guide rolls on guide shafts 252a to 252d. In this case, an operation button for controlling the operation of the motor may be provided to main-unit casing 110, and the user may operate the operation button as required. Further, in this case, a guide mechanism for guiding air tube 160 in a predetermined direction may separately be provided to retractor unit 250 or main-unit casing 110, so that air tube 160 is guided as the motor is operated and is fed automatically to the outside of main-unit casing 110. As the guide mechanism, a guide wall with which air tube 160 is in contact so that air tube 160 is guided in a predetermined direction, or a pair of a drive roller and a driven roller holding air tube 160 therebetween to guide air tube 160 in a predetermined direction, for example, may be used.

Third Embodiment

Figure 15:
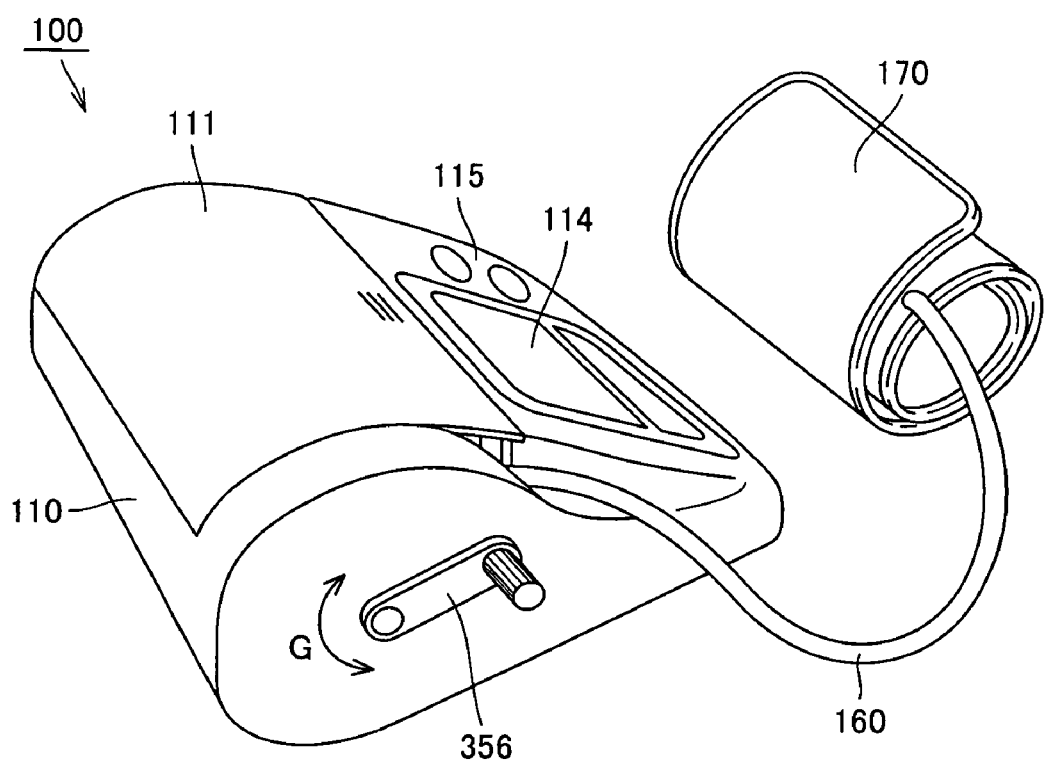
FIG. 15 is a perspective view showing an appearance of a blood pressure monitor according to a third embodiment of the present invention.

FIG. 15 is a perspective view of a blood pressure monitor according to a third embodiment of the present invention. Referring first to FIG. 15, an external structure of blood pressure monitor 100 in the present embodiment is described.

As shown in FIG. 15, blood pressure monitor 100 in the present embodiment differs from the blood pressure monitor in the first embodiment in that an open/close cover 111 is provided to cover a top surface of a rear portion of a main-unit casing 110 and a cuff housing is provided under open/close cover 111. On a top surface of a front portion of main-unit casing 110, a display unit 114 and an operation unit 115 are provided. In a left-side portion of main-unit casing 110, a retractor unit 350 (see FIGS. 16A, 16B, 17A and 17B) for an air tube 160 described hereinlater is provided. On a side surface of main-unit casing 110, a handle 356 of retractor unit 350 is provided. Other components are structured substantially similarly to those of the blood pressure monitor in the first embodiment and the detailed description thereof is not repeated here.

Figure 16A:
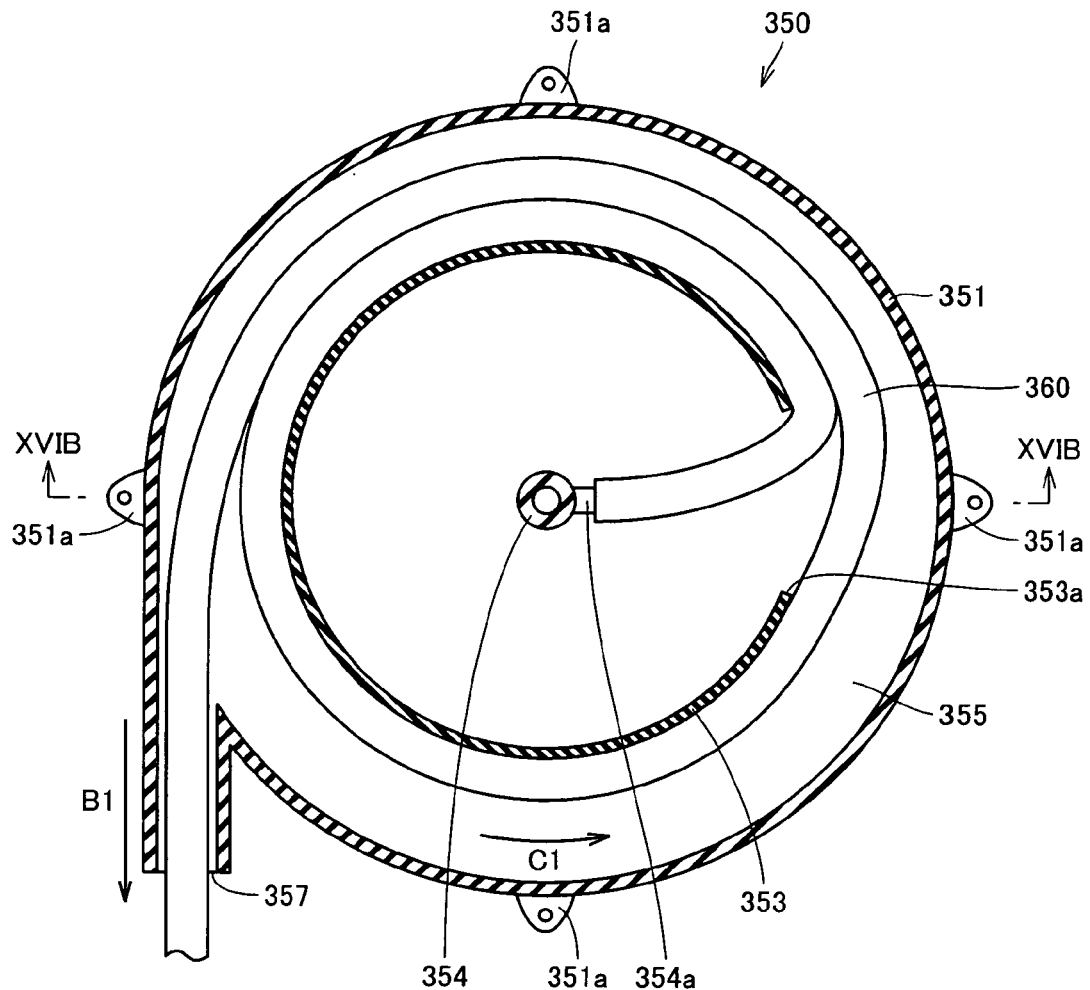
FIG. 16A is a schematic cross-sectional view showing the state where an air tube is drawn in into a retractor unit of the blood pressure monitor according to the third embodiment of the present invention.
Figure 16B:
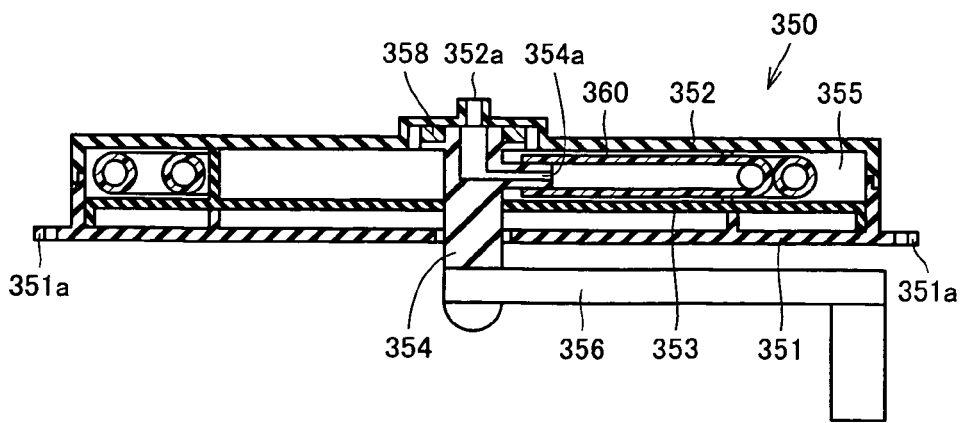
FIG. 16B is a schematic cross-sectional view along the line XVIB-XVIB shown in FIG. 16A.
Figure 17A:
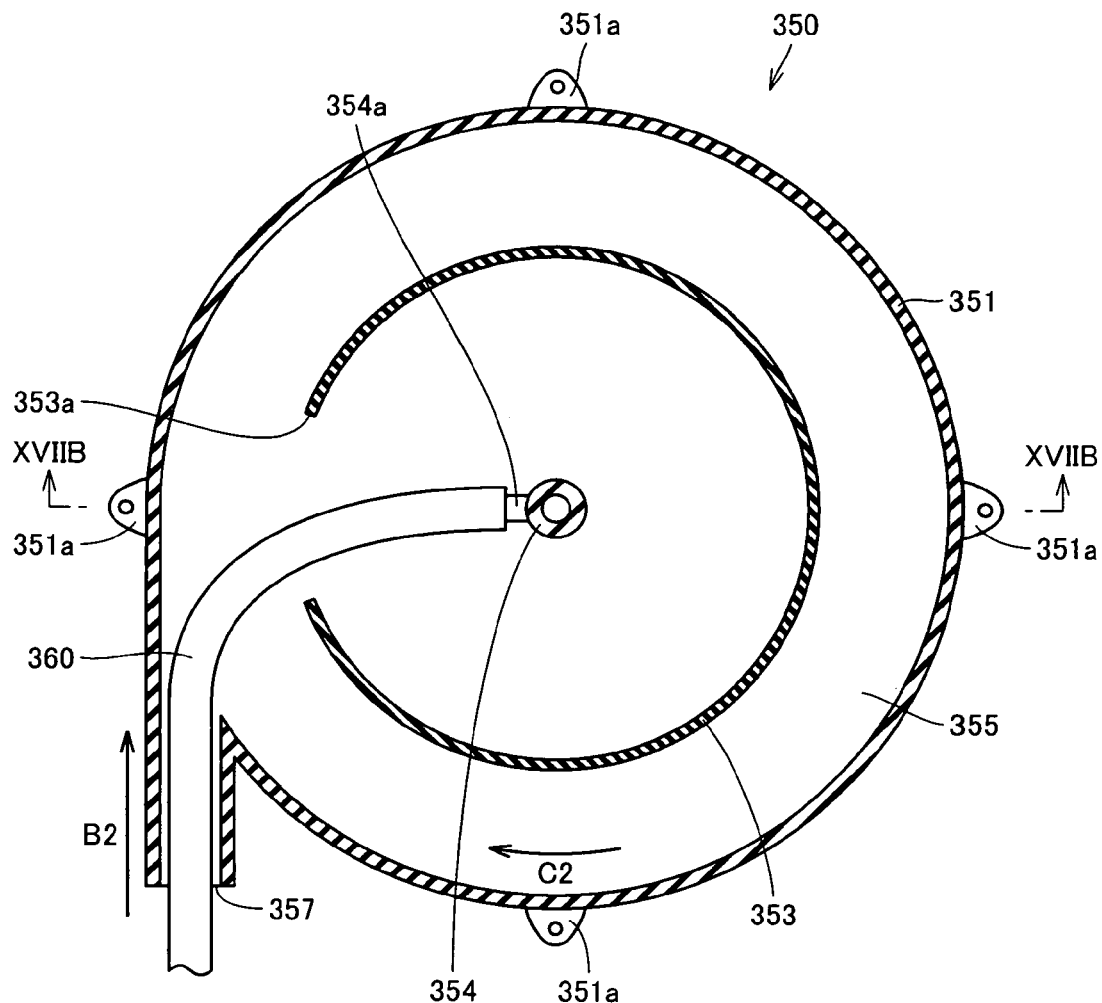
FIG. 17A is a schematic cross-sectional view showing the state where the air tube is drawn out from the retractor unit of the blood pressure monitor according to the third embodiment of the present invention.
Figure 17B:
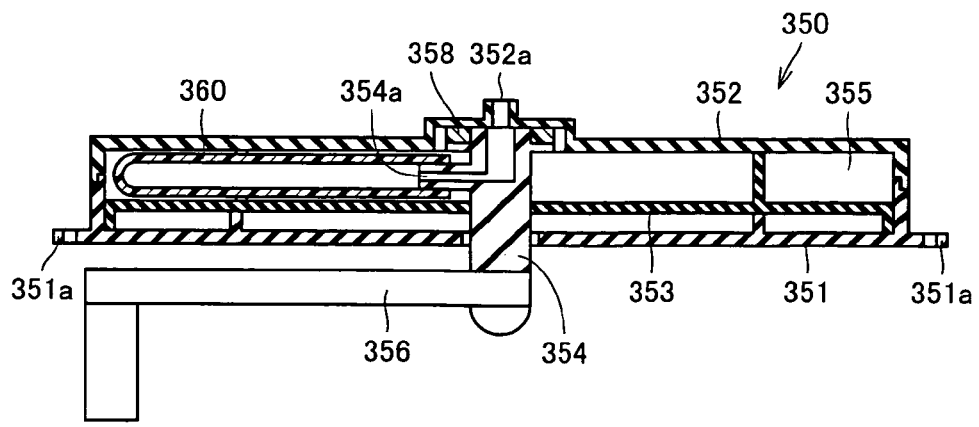
FIG. 17B is a schematic cross-sectional view along the line XVIIB-XVIIB shown in FIG. 17A.

FIGS. 16A, 16B, 17A and 17B illustrate a structure of the retractor unit as well as an operation of drawing out/drawing in the air tube of the blood pressure monitor in the present embodiment. FIGS. 16A and 16B show the case where the air tube is drawn in into the retractor unit, FIG. 16A is a cross-sectional view along a horizontal plane of the retractor unit and FIG. 16B is a cross-sectional view along the line XVIB-XVIB shown in FIG. 16A of the retractor unit. FIGS. 17A and 17B show the case where the air tube is drawn out from the retractor unit, FIG. 17A is a cross-sectional view along a horizontal plane of the retractor unit and FIG. 17B is a cross-sectional view along the line XVIIB-XVIIB shown in FIG. 17A of the retractor unit.

Referring first to FIGS. 16A, 16B, 17A and 17B, the structure of retractor unit 350 is described. As shown in FIGS. 16A, 16B, 17A and 17B, retractor unit 350 is formed by assembling a lower case 351 and an upper case 352 that constitute a shell, a bobbin 353 serving as a wound member, a shaft tube 354, and handle 356 serving as an rotational operation unit.

Lower case 351 is formed of a bottomed cylindrical member having a disk-shaped bottom surface, and has, on its outer periphery, a seizing portion 351a for fixing retractor unit 350 with respect to main-unit casing 110. Upper case 352 is formed of a bottomed cylindrical member having a disk-shaped bottom plate and has its central portion provided with a connection opening 352a. Connection opening 352a is a portion where an intermediate air tube 136 is connected in the state where retractor unit 350 is mounted on main-unit casing 110. Lower case 351 and upper case 352 are attached with respective opening surfaces facing each other and accordingly a space is formed inside the cases.

Bobbin 353 is rotatably provided in the space formed by lower case 351 and upper case 352. The space serves as an air tube housing 355 in which air tube 160 is housed.

Shaft tube 354 is fixed at a central portion of bobbin 353 and rotates together with bobbin 353. At an upper portion of shaft tube 354, a channel is provided having one end communicating with connection opening 352a provided in upper case 352. The other end of the channel communicates with a connection opening 354a formed to outwardly protrude from the peripheral surface of shaft tube 354. To this connection opening 354a, air tube 160 is connected. Between upper case 352 and shaft tube 354, such a seal member 358 as O ring is provided for ensuring airtightness.

Air tube 160 having one end attached to connection opening 354a of shaft tube 354 is drawn out toward the outside of bobbin 353 from a draw-out opening 353a provided in the peripheral surface of bobbin 353, and the drawn-out portion is wound on the peripheral surface of bobbin 353 in air tube housing 355. The other end of air tube 160 is drawn out to the outside of retractor unit 350 from an air-tube draw-out opening 357 provided at a predetermined position of the outer peripheral portion of lower case 351 and upper case 352.

To an end opposite to the end of shaft tube 354 that faces connection opening 352a, handle 356 as described above is fixed. Handle 356 can be rotated freely with respect to lower case 351 and upper case 352. As handle 356 is rotated in the direction indicated by the arrow G in the drawing, shaft tube 354 and bobbin 353 are rotated.

Next, the operation of drawing out/drawing in air tube 160 is described. As shown in FIGS. 16A and 16B, in the state where air tube 160 is housed in air tube housing 355, air tube 160 wound on bobbin 353 is housed in air tube housing 355. When air tube 160 is to be drawn out, the user rotates handle 356 provided on the outside of main-unit casing 110 in a predetermined direction, or holds a portion of air tube 160 that is drawn out of main-unit casing 110 to pull out air tube 160, so that bobbin 353 is rotated in the direction indicated by the arrow C1 in the drawing and air tube 160 is fed from air-tube draw-out opening 157 in the direction indicated by the arrow B1.

As shown in FIGS. 17A and 17B, in the state where air tube 160 is drawn out from air tube housing 355 to as much extent as possible, air tube 160 is not wound on bobbin 353. In this state, as the user rotates handle 356 in a predetermined direction (the direction opposite to the direction for drawing out air tube 160), bobbin 353 is rotated in the direction indicated by the arrow C2 in the drawing and accordingly air tube 160 is drawn in into retractor unit 350 via air-tube draw-out opening 357 in the direction indicated by the arrow B2 in the drawing, and is wound by means of bobbin 353.

In the blood pressure monitor having retractor unit 350 as described above, air tube 160 is easily and surely housed, by retractor unit 350, in air tube housing 355 provided in retractor unit 350, like the blood pressure monitor in the first embodiment. Therefore, the blood pressure monitor is superior in housing of air tube 160, particularly in ease of handling of air tube 160. Further, since air tube 160 is housed by means of retractor unit 350 in main-unit casing 110, it can be prevented that air tube 160 is bent or twisted for example to be broken.

Further, since air tube 160 wound on bobbin 353 is housed compactly in air tube housing 355, increase in size of retractor unit 350 can be prevented and retractor unit 350 can be formed with the relatively simple structure. Furthermore, since bobbin 353 is used to house air tube 160, the draw-out/draw-in operation can easily be implemented.

Moreover, since retractor unit 350 including handle 356 can also be used as a feed unit for feeding air tube 160, the blood pressure monitor can be made further superior in ease of handling. In addition, retractor unit 350 in the present embodiment is not structured to use elastic force for drawing in air tube 160. Therefore, even if air tube 160 is drawn out and the cuff is mounted on the left upper arm, no tension is exerted on the upper arm, the accuracy in measurement can be kept high and the user has to bear no burden.

Fourth Embodiment

Figure 18:
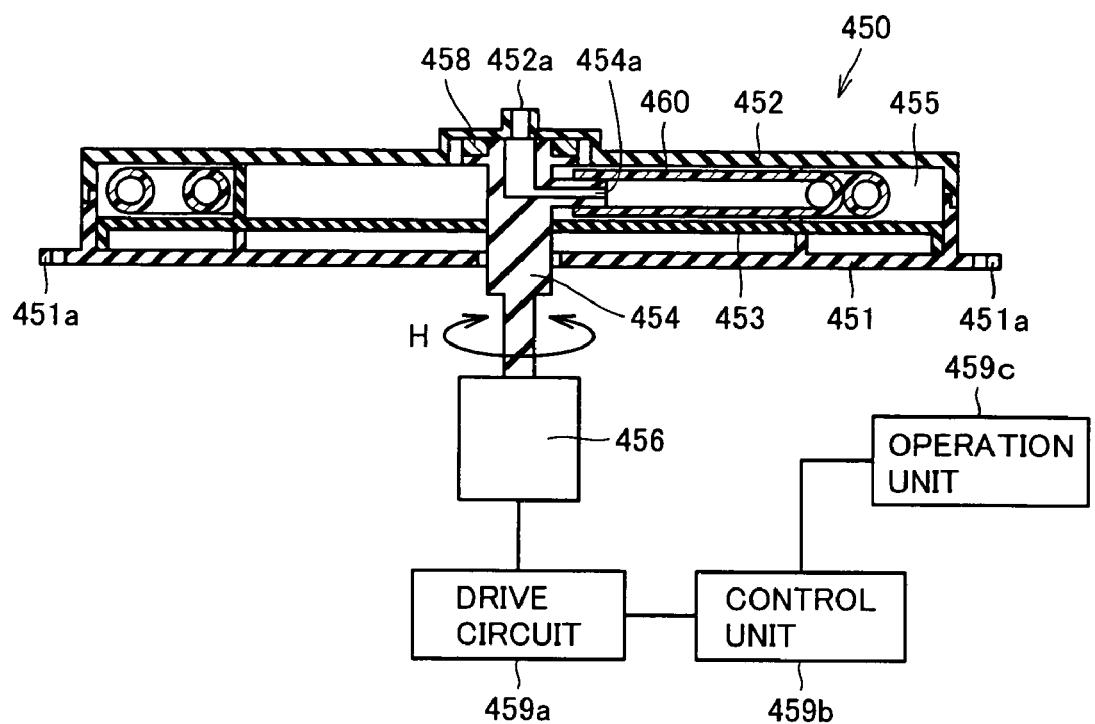
FIG. 18 is a schematic cross-sectional view of a retractor unit of a blood pressure monitor according to a fourth embodiment of the present invention.

FIG. 18 illustrates a structure of a retractor unit of a blood pressure monitor and an operation of drawing out/drawing in an air tube according to a fourth embodiment of the present invention, and is a schematic cross-sectional view of the retractor unit in the case where the air tube is drawn in into the retractor unit. The blood pressure monitor in the present embodiment is identical to the blood pressure monitor in the third embodiment except for the structure of the retractor unit, and the detailed description thereof is not repeated here. Further, most of the components of the retractor unit are common to these embodiments, a part of the description thereof is not repeated.

First, the structure of retractor unit 450 is described. As shown in FIG. 18, retractor unit 450 is formed by assembling a lower case 451 and an upper case 452 constituting a shell, a bobbin 453 serving as a wound member, a shaft tube 454, and a motor 456 serving as a drive unit. Lower case 451 and upper case 452 are attached in the manner that respective opening surfaces face each other. Thus, a space is formed within the cases and bobbin 453 is rotatably provided in this space. The space serves as an air tube housing 455 in which air tube 160 is housed. Shaft tube 454 is fixed at a central portion of bobbin 453 and is rotated together with bobbin 453.

Air tube 160 is drawn out, from a draw-out opening a provided in the peripheral surface of bobbin 453, toward the outside of bobbin 453, and a drawn-out portion of the air tube is wound on the peripheral surface of bobbin 453 in air tube housing 455. One end of air tube 160 is drawn out toward the outside of retractor unit 450 from an air tube draw-out opening-provided at a predetermined position of the outer peripheral portion of lower case 451 and upper case 452.

To the end of shaft tube 454 that is opposite to the end facing a connection opening 452a, motor 456 is attached. Motor 456 rotationally drives shaft tube 454 in the direction indicated by the arrow H in the drawing and thereby rotates bobbin 453. Motor 456 is driven by a drive circuit 459a and the rotating operation is controlled by a control unit 459b in accordance with operation of an operation unit 459c by the user.

Next, the operation of drawing out/drawing in air tube 160 is described. In the case where air tube 160 is to be drawn out from retractor unit 450, the user operates operation unit 459c and accordingly motor 456 rotationally drives shaft tube 454 in a predetermined direction. Thus, bobbin 453 is rotated in the predetermined direction and air tube 160 is fed from retractor unit 450. On the contrary, in the case where air tube 160 is to be drawn in into retractor unit 450, the user operates operation unit 459c and accordingly motor 456 rotationally drives shaft tube 454 in the opposite direction to the direction as described above. Thus, bobbin 453 is rotated in the direction opposite to the aforementioned direction, and air tube 160 is drawn in into retractor unit 450 and wound on bobbin 453.

The blood pressure monitor having retractor unit 450 as described above can also provide effects similar to those of the blood pressure monitor in the third embodiment. Further, since air tube 160 can be drawn out/drawn in by operating a button, which is easier than the operation of rotating the handle, the blood pressure monitor can be further superior in terms of convenience.

Fifth Embodiment

Figure 19:
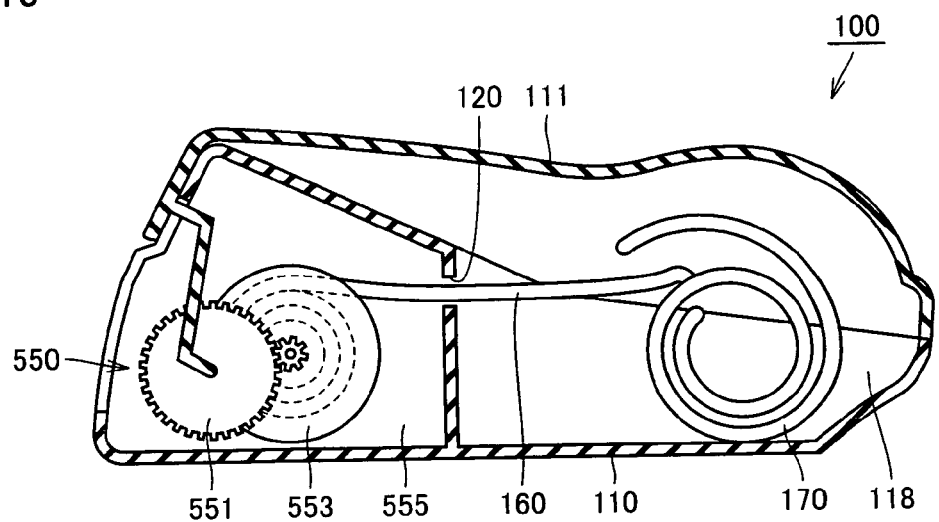
FIG. 19 shows the state where an air tube is drawn in into a retractor unit of a blood pressure monitor according to a fifth embodiment of the present invention.
Figure 20:
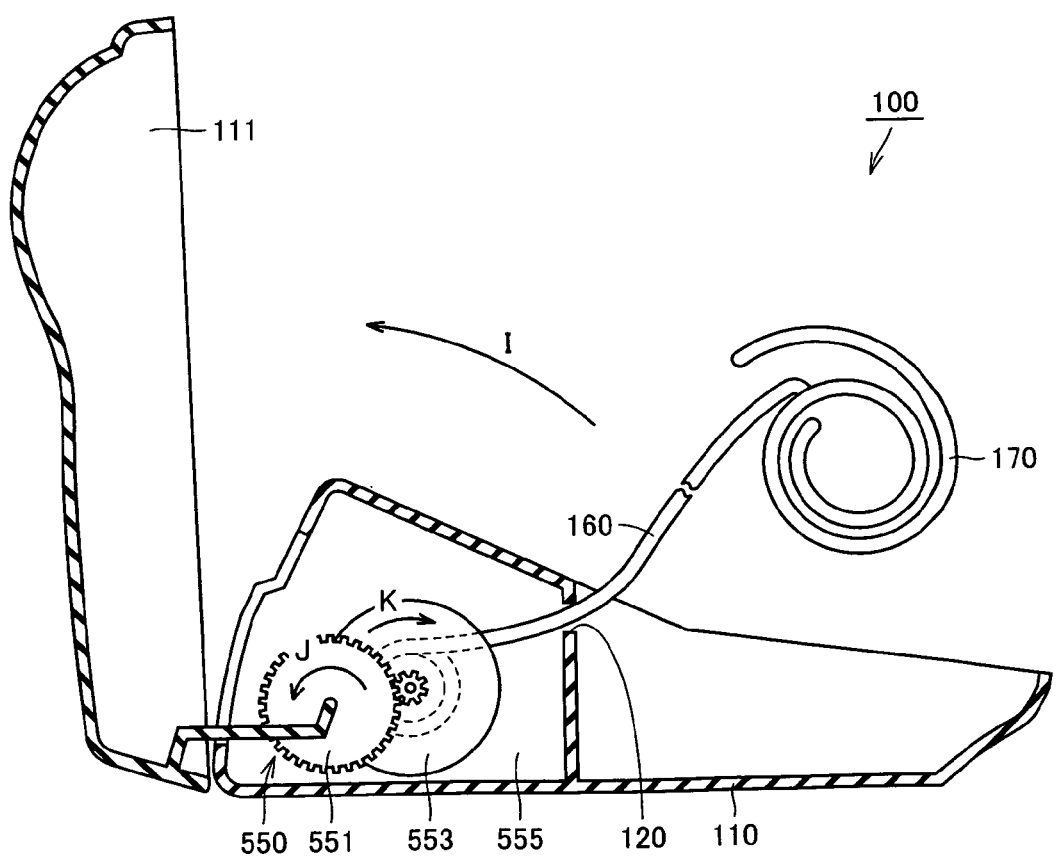
FIG. 20 shows the state where the air tube is drawn out from the retractor unit of the blood pressure monitor according to the fifth embodiment of the present invention.

FIGS. 19 and 20 illustrate a structure of a blood pressure monitor and an operation of drawing out/drawing in an air tube according to a fifth embodiment of the present invention. FIG. 19 is a schematic cross-sectional view of the retractor unit in the case where the air tube is drawn in into the retractor unit and FIG. 20 is a schematic cross-sectional view of the retractor unit in the case where the air tube is drawn out from the retractor unit. The blood pressure monitor in the present embodiment is identical to the blood pressure monitor in the first embodiment except for the structure of the retractor unit, and the detailed description thereof is not repeated here.

First, the structure of retractor unit 550 of the blood pressure monitor in the present embodiment is described. As shown in FIGS. 19 and 20, in blood pressure monitor 100 in the present embodiment, an air tube housing 555 for housing air tube 160 is provided in a rear portion of a main-unit casing 110, and retractor unit 550 is provided in this housing. Retractor unit 550 includes a gear 551 serving as a rotational force transmission mechanism that is rotated in interlocked manner as an open/close cover 111 is moved, and a bobbin 553 that is rotated in interlocked manner as gear 551 is rotated. On the peripheral surface of bobbin 553, air tube 160 is wound.

Next, the operation of drawing out/drawing in air tube 160 is described. In the case where air tube 160 is to be drawn out, in the state as shown in FIG. 19, the user opens open/close cover 111 in the direction indicated by the arrow I in FIG. 20. As open/close cover 111 is thus turned, gear 551 is rotated in the direction indicated by the arrow J in the drawing, and the rotation of gear 551 is transmitted to bobbin 553 to rotate bobbin 553 in the direction indicated by the arrow K in the drawing. As bobbin 553 is thus rotated, air tube 160 is fed from an opening 120 provided in a main-unit casing 110 to the outside of main-unit casing 110. On the contrary, in the case where air tube 160 is to be drawn in, the user closes open/close cover 111. As open/close cover 111 is thus turned, gear 551 is rotated in the direction opposite to the above-described direction, and the rotation of gear 551 is transmitted to bobbin 553 to rotate bobbin 553 in the direction opposite to the above-described direction. As bobbin 553 is thus rotated, air tube 160 is drawn in from opening 120 provided in main-unit casing 110 to the inside of main-unit casing 110, and is wound on bobbin 553.

In the blood pressure monitor having retractor unit 550 as described above, retractor unit 550 is used to easily and surely house air tube 160 in air tube housing 555 in which retractor unit 550 is disposed. Thus, the blood pressure monitor is superior in housing of air tube 160, particularly in terms of ease of handling of air tube 160. Further, since air tube 160 is housed in main-unit casing 110 by means of retractor unit 550, it can be prevented that air tube 160 is bent or twisted for example to be broken. In blood pressure monitor 100 in the present embodiment, air tube 160 is drawn out/drawn in interlocked manner as open/close cover 111 is opened/closed, and thus the blood pressure monitor is further superior in ease of handling.

Sixth Embodiment

Figure 21A:
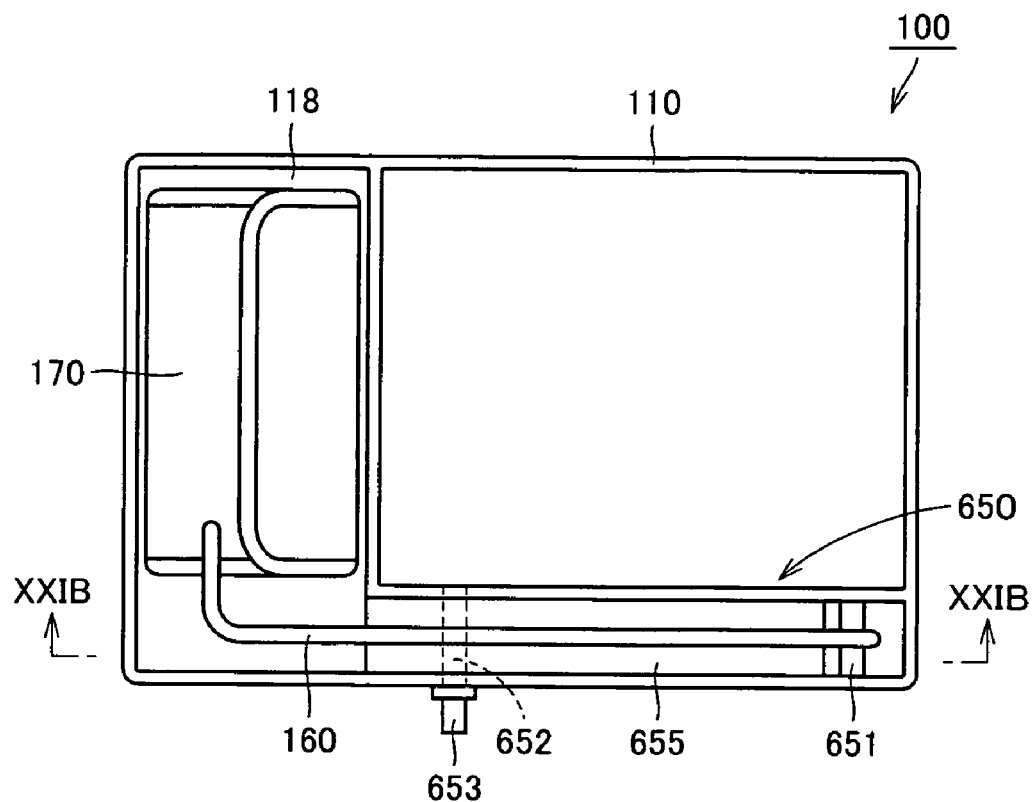
FIGS. 21A and 21B each show the state where an air tube is drawn in into a retractor unit of a blood pressure monitor according to a sixth embodiment of the present invention.
Figure 21B:
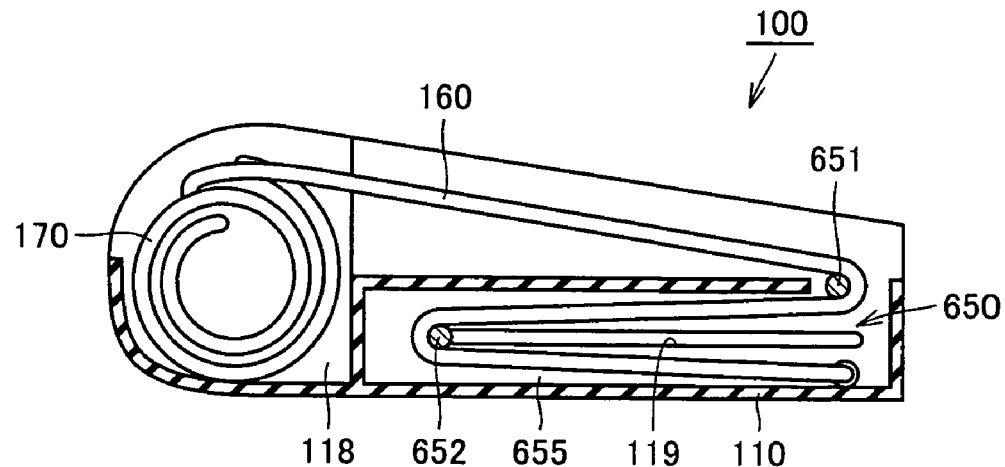
Figure 22A:
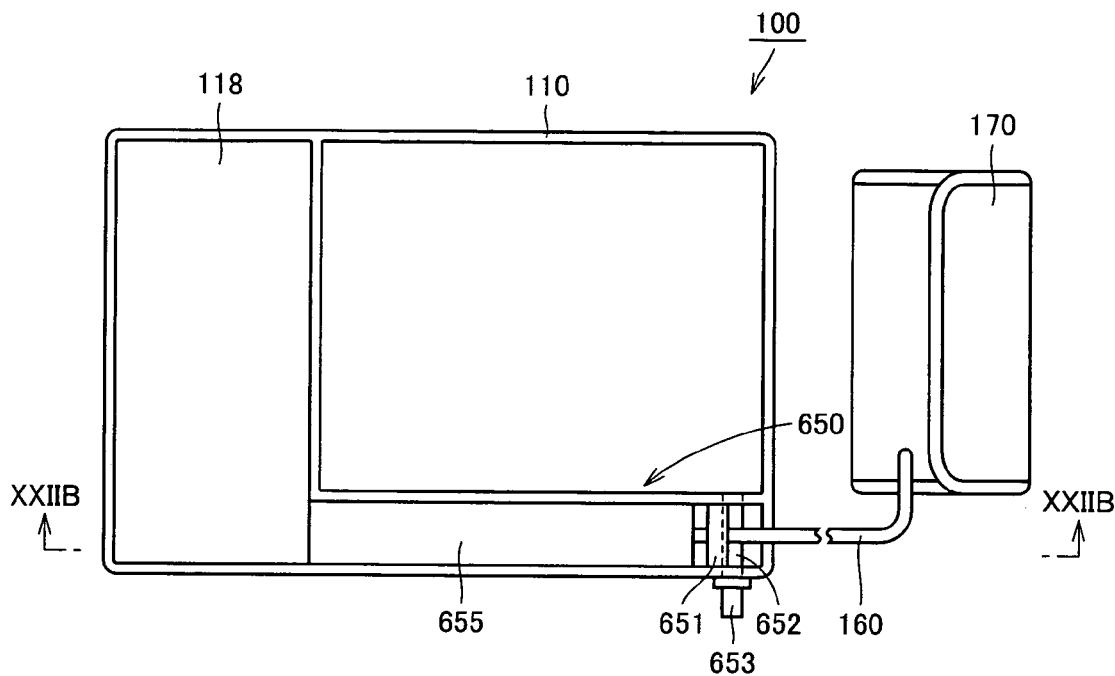
FIGS. 22A and 22B each show the state where the air tube is drawn out from the retractor unit of the blood pressure monitor according to the sixth embodiment of the present invention.
Figure 22B:
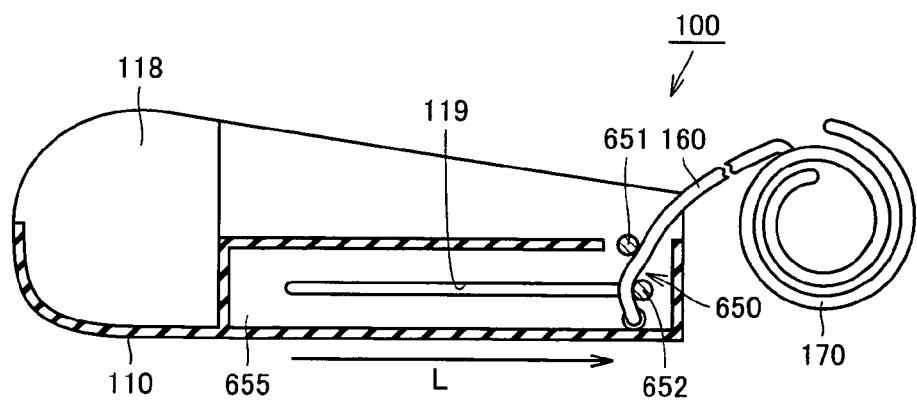

FIGS. 21A, 21B, 22A and 22B illustrate a structure of a blood pressure monitor and an operation of drawing out/drawing in an air tube according to a sixth embodiment of the present invention. FIGS. 21A and 21B show the case where the air tube is drawn in into a retractor unit, FIG. 21A is a top view and FIG. 21B is a cross-sectional view along the line XXIB-XXIB shown in FIG. 21A. FIGS. 22A and 22B show the case where the air tube is drawn out from the retractor unit, FIG. 22A is a top view and FIG. 22B is a cross-sectional view along the line XXIIB-XXIIB shown in FIG. 22A. The blood pressure monitor in the present embodiment is identical to the blood pressure monitor in the third embodiment except for the structure of the retractor unit, and the description thereof is not repeated here.

First, the structure of retractor unit 650 of the blood pressure monitor in the present embodiment is described. As shown in FIGS. 21A, 21B, 22A and 22B, in blood pressure monitor 100 in the present embodiment, an air tube housing 655 for housing air tube 160 is provided in a left side portion of a main-unit casing, and retractor unit 650 is disposed in this housing. Retractor unit 650 has catch portions 651, 652 by which air tube 160 can be caught. Of these catch portions, catch portion 651 is immovably fixed to main-unit casing 110 while catch portion 652 is mounted movably in a slit 119 provided to extend in the forward/backward direction in a wall surface of main-unit casing 110. Catch portion 652 is fixed to a slide lever 653 provided to protrude from a wall portion of main-unit casing 110. Slide lever 653 is slid in the forward/backward direction to cause catch portion 652 to slide in the forward/backward direction with respect to main-unit casing 110.

Next, the operation of drawing out/drawing in air tube 160 is described. In the case where air tube 160 is to be drawn out, in the state shown in FIGS. 21A and 21B, the user slides to move slide lever 653 toward the front of the main-unit casing (in the direction indicated by the arrow L in FIG. 22B). As the slide lever 653 is thus moved, catch portion 652 is moved in the direction indicated by the arrow L, so that the air tube housed in meandering state in air tube housing 655 can be drawn out. On the contrary, in the case where air tube 160 is to be drawn in, the user slides to move slide lever 653 in the direction opposite to the above-described direction. As slide lever 653 is thus moved, catch portion 652 is moved in the direction opposite to the above-described direction so as to draw air tube 160 into air tube housing 655 and house it in meandering state.

In the blood pressure monitor having retractor unit 650 as described above, retractor unit 650 is used to easily and surely house air tube 160 in air tube housing 655 in which retractor unit 650 is disposed. Thus, the blood pressure monitor is superior in housing of air tube 160, particularly ease of handling of air tube 160. Further, since air tube 160 is housed inside main-unit casing 110 by means of retractor unit 150, it can be prevented that air tube 160 is bent or twisted for example to be broken. In blood pressure monitor 100 in the present embodiment, the sliding operation of slide lever 653 can be used to draw out/draw in air tube 160 and thus the simple operation can be used to draw out/draw in the air tube.

Blood pressure monitor 100 in the present embodiment has been described in connection with the case as an example where the user holds and pulls air tube 160 to feed air tube 160 to the outside of main-unit casing 110. Alternatively, a guide mechanism may separately be provided to main-unit casing 110 for guiding air tube 160 in a predetermined direction. In this case, the guide mechanism may be structured to operate in interlocked manner as slide lever 653 is slid. Thus, as slide lever 653 is slid, air tube 160 can automatically be fed in interlocked manner to the outside of main-unit casing 110. As the guide mechanism, for example, a pair of a drive roller and a follower roller holding air tube 160 therebetween to guide the air tube 160 in a predetermined direction may be used.

Seventh Embodiment

Figure 23:
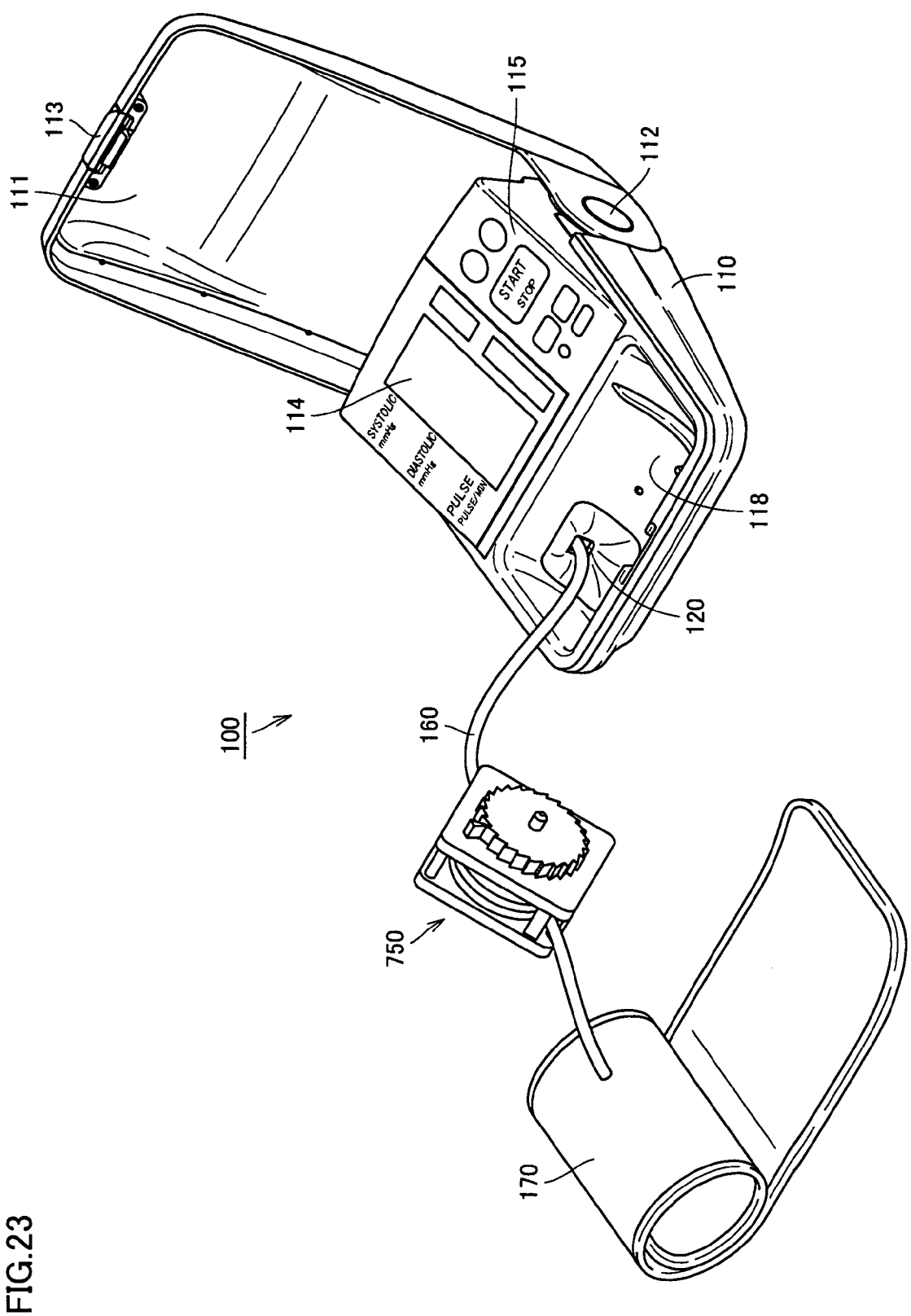
FIG. 23 is a perspective view showing an appearance of a blood pressure monitor and showing the state where a cuff is taken out of a main-unit casing while an open/close cover is opened, according to a seventh embodiment of the present invention.

FIG. 23 is a perspective view showing an appearance of a blood pressure monitor and showing the state where a cuff is removed from a main-unit casing while an open/close cover is opened, according to a seventh embodiment of the present invention. The blood pressure monitor in the present embodiment is identical to the blood pressure monitor in the first embodiment except for the structure of the retractor unit, and the description except for the description of the components concerning the retractor unit is not repeated here.

As shown in FIG. 23, regarding blood pressure monitor 100 in the present embodiment, retractor unit 750 serving as a retraction mechanism is provided outside main-unit casing 110. Specifically, the retractor unit is provided at any position of air tube 160. While the blood pressure monitor is not used, retractor unit 750 is housed together with a cuff 170 in a cuff casing 118 provided in a front portion of main-unit casing 110.

Figure 25A:
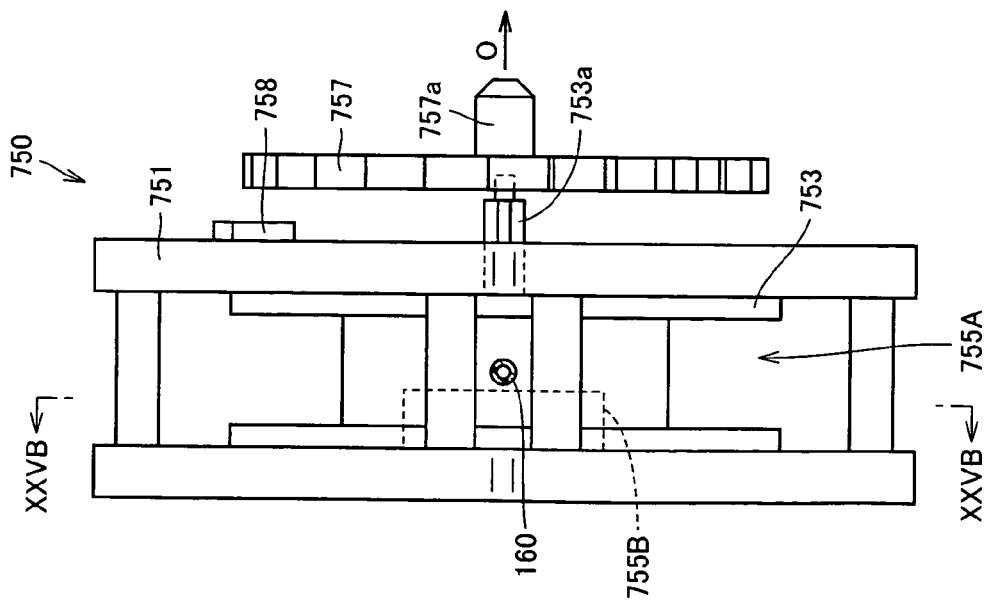
FIGS. 25A and 25B each show the state where the air tube is drawn out from the retractor unit of the blood pressure monitor, according to the seventh embodiment of the present invention.
Figure 25B:
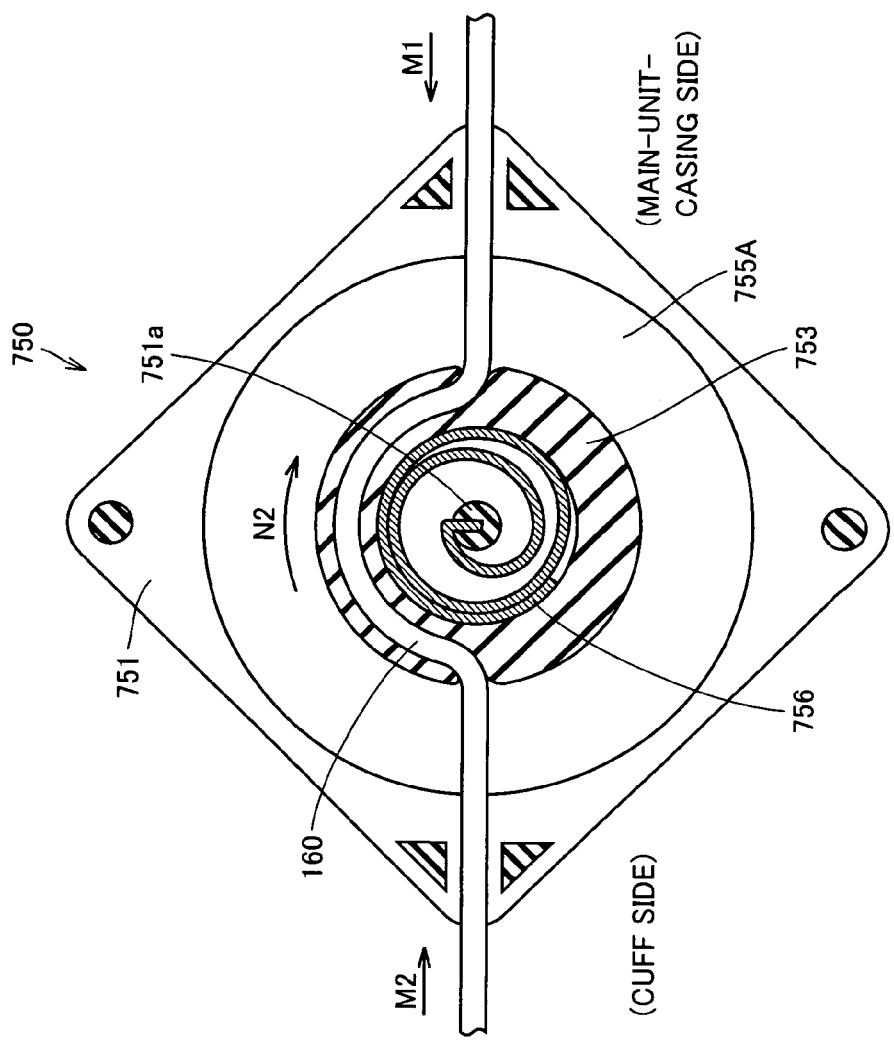

FIGS. 24A, 24B, 25A and 25B illustrate a structure of the retractor unit of the blood pressure monitor and an operation of drawing out/drawing in the air tube according to the present embodiment. FIGS. 24A and 24B show the case where the air tube is drawn in into the retractor unit. FIG. 24A is a cross-sectional view of the retractor unit and FIG. 24B is a side view of the retractor unit. FIGS. 25A and 25B show the case where the air tube is drawn out from the retractor unit. FIG. 25A is a cross-sectional view of the retractor unit and FIG. 25B is a side view of the retractor unit.

First, referring to FIGS. 24A, 24B, 25A and 25B, the structure of retractor unit 750 is described. As shown in FIGS. 24A, 24B, 25A and 25B, retractor unit 750 is formed by assembling a case 751 forming a shell, a bobbin 753 serving as a wound member and a spiral spring 756 serving as an elastic member.

Case 751 is structured in the manner that two plate members almost rectangular in shape are disposed in parallel with each other and support struts coupling these two plate members are provided to form a space on the inside. The space corresponds to an air tube housing 755A in which air tube 160 is housed. At a central portion of case 751, a shaft 751a is provided that extends to protrude from one of the plate members to the other plate member. Bobbin 753 is rotatably provided in the space formed between the two plate members and has a spring housing 755B therein. In spring housing 755B, spiral spring 756 is housed.

In bobbin 753, a hole is made in which air tube 160 is passed. Thus, air tube 160 is drawn out from respective positions opposite to each other on the peripheral surface of bobbin 753. One end of air tube 160 that is drawn out from bobbin 753 is connected to an inflation/deflation mechanism provided to main-unit casing 110 and the other end is connected to air bag 171 contained in cuff 170.

To one plate member of case 751, a disk-shaped toothed plate 757 is attached. Toothed plate 757 is pressed by such an elastic member as spring (not shown) against case 751. At a central portion of toothed plate 757, a knob 757a is provided. At a predetermined position of the plate member of case 751 to which toothed plate 757 is attached, a stopper 758 serving as an air tube locking mechanism is provided. Stopper 758 is engaged with any teeth provided on the outer peripheral surface of toothed plate 757 to restrict rotation in one direction of toothed plate 757. To bobbin 753, a rotation transmitting portion 753a having its cross section in the shape of a cross and protruding toward toothed plate 757 is provided. The leading end of the rotation transmitting portion is engaged with a cross-shaped groove provided at a substantially central portion of toothed plate 757. Thus, stopper 758 locks bobbin 753 via toothed plate 757 so that bobbin 753 can be rotated in one direction only and thereby indirectly locks air tube 160.

Spiral spring 756 is housed in spring housing 755B and has one end fixed to shaft portion 751a of case 751 and the other end fixed at a predetermined position of the inner peripheral surface of bobbin 753.

Next, the operation of drawing out/drawing in air tube 160 is described. As shown in FIGS. 24A and 24B, in the state where air tube 160 is housed in air tube housing 755A, air tube 160 wound on bobbin 753 is housed in air tube housing 755A. In this state, no external force is exerted on spiral spring 756, and spiral spring 756 is substantially free. When air tube 160 is to be drawn out, the user holds air tube 160 drawn out from retractor unit in the directions opposite to each other, and pulls air tube 160 outwardly. Accordingly, air tube 160 is pulled in respective directions indicated by the arrows M1 and M2 in the drawing to cause bobbin 753 to rotate in the direction indicated by the arrow N1, and air tube 160 is fed to the outside of retractor unit 750. The rotational direction of bobbin 753 at this time is opposite to the direction in which the rotation of bobbin 753 is restricted by stopper 758 and thus air tube 160 can be drawn out without restriction on the rotation of bobbin 753.

As bobbin 753 is rotated, a force in the rotational direction is also exerted on spiral spring 756 having one end fixed to the inner peripheral surface of bobbin 753, and the force causes spiral spring 756 to elastically deform. As spiral spring 756 is elastically deformed, a resilient force is generated at spiral spring 756. However, the presence of stopper 758 allows air tube 160 to be locked in the state where air tube 160 is drawn out to a desired extent from retractor unit 750.

As shown in FIGS. 25A and 25B, in the state where air tube 160 is drawn out from air tube housing 755A to as much extent as possible, air tube 160 is not wound on bobbin 753 and the above-described resilient force is generated at spiral spring 756. In this state, when the user holds knob 757a of toothed plate 757 and pulls the knob in the direction indicated by the arrow O as shown in FIG. 25A, the engagement between the cross-shaped groove provided in toothed plate 757 and rotation transmitting portion 753a having a cross section in the shape of a cross is released. Then, the resilient force of spiral spring 756 causes bobbin 753 to rotate in the direction indicated by the arrow N2 in FIG. 25B, and accordingly air tube 160 is drawn in the directions indicated by the arrows M1 and M2. Air tube 160 as drawn in is wound on bobbin 753 in retractor unit 750.

As described above, regarding blood pressure monitor 100 in the present embodiment, retractor unit 750 is used to easily and surely house air tube 160 in air tube housing 755A provided in retractor unit 750. Thus, the blood pressure monitor is superior in housing of air tube 160, particularly in ease of handling of air tube 160. Further, since air tube 160 is housed in retractor unit 750, it can be prevented that air tube 160 is bent or twisted for example to be broken.

Moreover, since air tube 160 is housed compactly in the state where the air tube is wound on bobbin 753 in air unit housing 755A, increase in size of retractor unit 750 can be prevented and the relatively simple structure can be used to form retractor unit 750. Further, since bobbin 753 is used for housing air tube 160, the air tube can easily be drawn out/drawn in.

In addition, since the elastic force of spiral spring 756 can be used to draw in air tube 160, the blood pressure monitor can be made superior in ease of handling of air tube 160. Further, since stopper 758 serving as the air tube locking mechanism can be used to lock air tube 160 in the state where the extent to which air tube 160 is drawn out is adjusted to an arbitrary extent, the blood pressure monitor can be made superior in terms of convenience. Furthermore, in the state where air tube 160 is drawn out and the cuff is mounted on the left upper arm, the air tube locking mechanism can prevent the resilient force of spiral spring 756 from being exerted on the upper arm, and thus the accuracy in measurement can be kept high and the user has to bear no burden.

In connection with the first to seventh embodiments each, the oscillometric blood pressure monitor is described as an example. However, it would naturally be understood that the present invention is also applicable to a blood pressure monitor using the Korotkoff method. In this case, a signal line provided to connect the main-unit casing and the cuff may be integrated with the air tube into a composite line or these signal line and air tube may separately be provided.

The air tube locking mechanism described above in connection with the first embodiment is structured to lock the air tube by means of the frictional force exerted on the air tube. Alternatively, a latch mechanism that locks rotation of the bobbin in stepwise manner may be provided to the retractor unit for locking the air tube.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A blood pressure measuring device comprising:
   a cuff having an inflatable/deflatable fluid bag;
   a main-unit casing in which an inflation/deflation mechanism inflating/deflating said fluid bag is disposed;
   a flexible connection tube connecting said fluid bag and said inflation/deflation mechanism and having a stopper portion preventing a cuff-side tube portion of said connection tube from being drawn into said main-unit casing; and
   a retraction mechanism capable of drawing in said connection tube that is drawn out from said main-unit casing, into a connection tube housing provided in said main-unit casing, wherein
   in a state where said connection tube is housed to as much extent as possible in said connection tube housing by said retraction mechanism, at least a part of said connection tube is located on the outside of said main-unit casing,
   said main-unit casing has an opening for drawing out said connection tube,
   said stopper portion abuts on a periphery of said opening and thereby prevents said connection tube from being further drawn in into said main-unit casing,
   said cuff-side tube portion of said connection tube has one end connected to said fluid bag,
   said connection tube includes a main-unit-casing-side tube portion having one end connected to said inflation/deflation mechanism and a connector connecting the other end of said cuff-side tube portion and the other end of said main-unit-casing-side tube portion, and
   said stopper portion is formed of said connector.

2. The blood pressure measuring device according to claim 1, wherein
   said retraction mechanism has a winding member on which said connection tube that is drawn in into said connection tube housing is wound.

3. The blood pressure measuring device according to claim 2, wherein
   said retraction mechanism has an elastic member coupled to said winding member, and
   elastic force of said elastic member rotationally drives said winding member and thereby causes said connection tube to be drawn in into said connection tube housing.

4. The blood pressure measuring device according to claim 3, further comprising a connection tube locking mechanism locking said connection tube against the elastic force of said elastic member.

5. The blood pressure measuring device according to claim 2, wherein
   said retraction mechanism has a drive unit coupled to said winding member, and
   drive force of said drive unit rotationally drives said winding member and thereby causes said connection tube to be drawn in into said connection tube housing.

6. The blood pressure measuring device according to claim 2, wherein
   said retraction mechanism has a rotational operation unit coupled to said winding member, and
   rotational operation of said rotational operation unit rotationally drives said winding member and thereby causes said connection tube to be drawn in into said connection tube housing.

7. The blood pressure measuring device according to claim 1, wherein
   said retraction mechanism includes an elastic member, and
   elastic force of said elastic member causes said connection tube to be drawn in into said connection tube housing.

8. The blood pressure measuring device according to claim 1, wherein
   said retraction mechanism includes a drive unit, and
   drive force of said drive unit causes said connection tube to be drawn in into said connection tube housing.

9. The blood pressure measuring device according to claim 1, wherein
   an opening provided in said main-unit casing for drawing out said connection tube is opened toward a front side of said main-unit casing.

10. The blood pressure measuring device according to claim 9, wherein
    said cuff is to be mounted on a left upper arm portion of a subject, and said opening is provided at a central portion or a left-side portion of said main-unit casing as said main-unit casing is seen from the front side.

11. The blood pressure measuring device according to claim 9, wherein
    said cuff is to be mounted on a right upper arm portion of a subject, and said opening is provided at a central portion or a right-side portion of said main-unit casing as said main-unit casing is seen from the front side.

12. The blood pressure measuring device according to claim 9, wherein
    said main-unit casing has, at its front portion, a cuff housing for housing said cuff, and
    said opening is provided in said cuff housing.

13. The blood pressure measuring device according to claim 1, wherein
    said retraction mechanism is horizontally disposed in said main-unit casing and a main surface of said retraction mechanism is parallel with a bottom surface of said main-unit casing.

14. The blood pressure measuring device according to claim 1, wherein
    said main-unit casing includes:
    display and operation units positioned in an upper surface and at a rear portion of said main-unit casing;
    a cuff housing for housing said cuff, wherein a depressed front portion of said main-unit housing forming said cuff housing; and
    a hingedly attached cover positionable in a closed position to cover said display and operation units and said cuff housing.

* * * * *

UNITED STATES PATENT AND TRADEMARK OFFICE
CERTIFICATE OF CORRECTION

PATENT NO. : 7,722,543 B2  
APPLICATION NO. : 11/502394  
DATED : May 25, 2010  
INVENTOR(S) : Hiroshi Kishimoto et al.

Page 1 of 1

It is certified that error appears in the above-identified patent and that said Letters Patent is hereby corrected as shown below:

On the Title page:

Under Section (56) U.S. PATENT DOCUMENTS, please add:

--2004/0010198 A1   1/2004   Yamakoshi et al.--

Under Section (56) FOREIGN PATENT DOCUMENTS, please add:

--EP 1 752 090   2/2007--

Under Section (56) OTHER PUBLICATIONS, please add:

--Russian Office Action dated December 18, 2007, directed to counterpart Russian Application No. 2006129230/14; 18 pages--

Signed and Sealed this  
Twenty-ninth Day of March, 2011

David J. Kappos  
*Director of the United States Patent and Trademark Office*